United States Patent
Ben-Haim et al.

(10) Patent No.: US 8,219,201 B2
(45) Date of Patent: *Jul. 10, 2012

(54) SMOOTH MUSCLE CONTROLLER FOR CONTROLLING THE LEVEL OF A CHEMICAL IN THE BLOOD STREAM

(75) Inventors: Shlomo Ben-Haim, Haifa (IL); Nissim Darvish, Haifa (IL); Yuval Mika, Haifa (IL); Maier Fenster, Petach Tikva (IL); Bella Felzen, Haifa (IL); Isaac Shemer, Ramat-Gan (IL)

(73) Assignee: Metacure Limited, Hamilton (BM)

( * ) Notice: Subject to any disclaimer, the term of this patent is extended or adjusted under 35 U.S.C. 154(b) by 797 days.

This patent is subject to a terminal disclaimer.

(21) Appl. No.: 11/736,183

(22) Filed: Apr. 17, 2007

(65) Prior Publication Data

US 2007/0185540 A1  Aug. 9, 2007

Related U.S. Application Data

(60) Division of application No. 10/282,968, filed on Oct. 29, 2002, now Pat. No. 7,221,978, which is a division of application No. 09/481,253, filed on Jan. 11, 2000, now Pat. No. 6,571,127, which is a continuation of application No. PCT/IL97/00243, filed on Jul. 16, 1997.

(51) Int. Cl.
*A61N 1/32* (2006.01)

(52) U.S. Cl. .............................. 607/40; 607/2

(58) Field of Classification Search ........................ None
See application file for complete search history.

(56) References Cited

U.S. PATENT DOCUMENTS

| 1,918,386 A | 7/1933 | Esau |
| 2,593,067 A | 4/1952 | Spencer |
| 3,541,390 A | 11/1970 | Jahnke |
| 3,650,277 A | 3/1972 | Sjostrand et al. |
| 3,658,051 A * | 4/1972 | MacLean ........................ 600/14 |
| 3,911,930 A | 10/1975 | Hagfors et al. |
| 3,933,147 A | 1/1976 | Du Vall et al. |
| 4,165,454 A | 8/1979 | Carlsson et al. |
| 4,337,776 A | 7/1982 | Daly et al. |
| 4,342,896 A | 8/1982 | Teich |

(Continued)

FOREIGN PATENT DOCUMENTS

EP    0268379    5/1988

(Continued)

OTHER PUBLICATIONS

Devedeux et al. "Uterine Electromyography: A Critical Review", American Journal of Obstetric Gynecology, 169: 1636-1653, 1993.

(Continued)

*Primary Examiner* — Kennedy J Schaetzle
(74) *Attorney, Agent, or Firm* — William H. Dippert; Eckert Seamans Cherin & Mellott, LLC

(57) ABSTRACT

An apparatus that comprises at least one electrode adapted to be placed adjacent to a portion of smooth muscle (200) and a controller for electrifying the electrode with a non-excitatory electric field (210) which does not generate excitation of the smooth muscle. The non-excitatory electric field affects the activity of the smooth muscle in a manner that controls a level of a chemical in the blood stream.

21 Claims, 14 Drawing Sheets

U.S. PATENT DOCUMENTS

| | | | |
|---|---|---|---|
| 4,354,153 A | 10/1982 | Lentz | |
| 4,377,733 A | 3/1983 | Yamaguchi et al. | |
| 4,406,288 A | 9/1983 | Horwinski et al. | |
| 4,411,268 A | 10/1983 | Cox | |
| 4,431,888 A | 2/1984 | Simpson | |
| 4,447,693 A | 5/1984 | Buck | |
| 4,475,024 A | 10/1984 | Tateda | |
| 4,537,195 A | 8/1985 | McDonnell | |
| 4,537,203 A | 8/1985 | Machida | |
| 4,552,150 A | 11/1985 | Zacouto | |
| 4,554,922 A | 11/1985 | Prystowsky et al. | |
| 4,554,992 A | 11/1985 | Kassai | |
| 4,596,915 A | 6/1986 | Simpson | |
| 4,873,986 A | 10/1989 | Wallace | |
| 5,025,787 A | 6/1991 | Sutherland et al. | |
| 5,026,397 A | 6/1991 | Aoki et al. | |
| 5,031,617 A * | 7/1991 | Klettner | 607/2 |
| 5,083,564 A | 1/1992 | Scherlag | |
| 5,083,565 A | 1/1992 | Parins | |
| 5,087,243 A | 2/1992 | Avitall | |
| 5,097,833 A | 3/1992 | Campos | |
| 5,133,354 A | 7/1992 | Kallok | |
| 5,144,554 A | 9/1992 | Zhang et al. | |
| 5,188,104 A | 2/1993 | Wernicke et al. | |
| 5,202,095 A | 4/1993 | Houchin et al. | |
| 5,205,284 A | 4/1993 | Freeman | |
| 5,231,988 A | 8/1993 | Wernicke et al. | |
| 5,236,413 A | 8/1993 | Feiring | |
| 5,292,344 A | 3/1994 | Douglas | |
| 5,320,642 A | 6/1994 | Scherlag | |
| 5,397,344 A | 3/1995 | Garfield et al. | |
| 5,415,629 A | 5/1995 | Henley | |
| 5,423,872 A | 6/1995 | Cigaina | |
| 5,445,609 A | 8/1995 | Lattin et al. | |
| 5,447,526 A | 9/1995 | Karsdon | |
| 5,451,751 A | 9/1995 | Takimoto et al. | |
| 5,501,662 A | 3/1996 | Hofmann | |
| 5,540,730 A | 7/1996 | Terry, Jr. et al. | |
| 5,552,150 A | 9/1996 | Horrobin et al. | |
| 5,556,760 A | 9/1996 | Nakamura et al. | |
| 5,562,720 A | 10/1996 | Stern et al. | |
| 5,616,268 A | 4/1997 | Carr | |
| 5,634,895 A | 6/1997 | Igo et al. | |
| 5,634,899 A | 6/1997 | Shapland et al. | |
| 5,690,691 A | 11/1997 | Chen et al. | |
| 5,727,558 A | 3/1998 | Hakki et al. | |
| 5,779,661 A | 7/1998 | Stephen et al. | |
| 5,800,464 A | 9/1998 | Kieval | |
| 5,814,079 A | 9/1998 | Kieval | |
| 5,861,014 A | 1/1999 | Familoni | |
| 5,871,506 A | 2/1999 | Mower | |
| 5,919,216 A | 7/1999 | Houben et al. | |
| 5,925,070 A | 7/1999 | King et al. | |
| 5,961,871 A | 10/1999 | Bible et al. | |
| 5,962,246 A | 10/1999 | Ladner et al. | |
| 5,991,649 A | 11/1999 | Garfield et al. | |
| 5,995,872 A | 11/1999 | Bourgeois | |
| 6,023,640 A | 2/2000 | Ross | |
| 6,026,326 A | 2/2000 | Bardy | |
| 6,026,626 A | 2/2000 | Fisher | |
| 6,083,249 A | 7/2000 | Familoni | |
| 6,096,361 A | 8/2000 | Yamane et al. | |
| 6,135,978 A | 10/2000 | Houben et al. | |
| 6,135,987 A | 10/2000 | Tsai et al. | |
| 6,141,587 A | 10/2000 | Mower | |
| 6,243,607 B1 | 6/2001 | Mintchev et al. | |
| 6,298,268 B1 | 10/2001 | Ben-Haim et al. | |
| 6,363,279 B1 | 3/2002 | Ben-Haim et al. | |
| 6,381,495 B1 | 4/2002 | Jenkins | |
| 6,449,511 B1 | 9/2002 | Mintchev et al. | |
| 6,463,323 B1 | 10/2002 | Conrad et al. | |
| 6,476,766 B1 | 11/2002 | Cohen | |
| 6,571,127 B1 | 5/2003 | Ben-Haim et al. | |
| 6,594,515 B2 | 7/2003 | Watson | |
| 6,600,953 B2 | 7/2003 | Flesler et al. | |
| 6,658,297 B2 | 12/2003 | Loeb | |
| 6,684,104 B2 | 1/2004 | Gordon et al. | |
| 6,810,286 B2 | 10/2004 | Donovan et al. | |
| 6,832,114 B1 | 12/2004 | Whitehurst et al. | |
| 6,947,792 B2 * | 9/2005 | Ben-Haim et al. | 607/2 |
| 6,949,081 B1 | 9/2005 | Chance | |
| 6,993,391 B2 | 1/2006 | Flesler et al. | |
| 7,006,871 B1 | 2/2006 | Darvish et al. | |
| 7,092,753 B2 | 8/2006 | Darvish et al. | |
| 7,120,497 B2 | 10/2006 | Ben-Haim et al. | |
| 7,171,263 B2 | 1/2007 | Darvish et al. | |
| 7,190,997 B1 | 3/2007 | Darvish et al. | |
| 7,221,978 B2 | 5/2007 | Ben-Haim et al. | |
| 7,966,071 B2 * | 6/2011 | Ben-Haim et al. | 607/40 |
| 2002/0026141 A1 | 2/2002 | Houben et al. | |
| 2002/0161414 A1 | 10/2002 | Flesler et al. | |
| 2002/0162836 A1 | 11/2002 | Taino et al. | |
| 2003/0055464 A1 | 3/2003 | Darvish et al. | |
| 2003/0055465 A1 | 3/2003 | Ben-Haim et al. | |
| 2003/0055466 A1 | 3/2003 | Ben-Haim et al. | |
| 2003/0055467 A1 | 3/2003 | Ben-Haim et al. | |
| 2003/0208242 A1 | 11/2003 | Harel et al. | |
| 2004/0044376 A1 | 3/2004 | Flesler et al. | |
| 2004/0059393 A1 | 3/2004 | Policker et al. | |
| 2004/0134904 A1 | 7/2004 | Clemen, Jr. | |
| 2004/0147816 A1 | 7/2004 | Policker et al. | |
| 2004/0158289 A1 | 8/2004 | Girouard et al. | |
| 2004/0232140 A1 | 11/2004 | Kanzaki et al. | |
| 2004/0249421 A1 | 12/2004 | Harel et al. | |
| 2005/0192542 A1 | 9/2005 | Dev et al. | |
| 2006/0074459 A1 | 4/2006 | Flesler et al. | |
| 2006/0085045 A1 | 4/2006 | Harel et al. | |
| 2006/0184207 A1 | 8/2006 | Darvish et al. | |
| 2007/0027487 A1 | 2/2007 | Mika et al. | |
| 2007/0027493 A1 | 2/2007 | Ben-Haim et al. | |
| 2007/0051849 A1 | 3/2007 | Watts et al. | |
| 2007/0060812 A1 | 3/2007 | Harel et al. | |
| 2007/0060971 A1 | 3/2007 | Glasberg et al. | |
| 2007/0092446 A1 | 4/2007 | Haddad et al. | |
| 2007/0156177 A1 | 7/2007 | Harel et al. | |
| 2007/0161851 A1 | 7/2007 | Takizawa et al. | |
| 2007/0179556 A1 | 8/2007 | Ben Haim et al. | |
| 2007/0185540 A1 | 8/2007 | Ben-Haim et al. | |
| 2007/0293901 A1 | 12/2007 | Rousso et al. | |
| 2007/0299320 A1 | 12/2007 | Policker et al. | |
| 2008/0051849 A1 | 2/2008 | Ben-Haim et al. | |
| 2008/0058889 A1 | 3/2008 | Ben-Haim et al. | |
| 2008/0058891 A1 | 3/2008 | Ben-Haim et al. | |
| 2008/0065168 A1 | 3/2008 | Bitton et al. | |
| 2008/0178684 A1 | 7/2008 | Spehr | |
| 2009/0062893 A1 | 3/2009 | Spehr | |
| 2009/0088816 A1 | 4/2009 | Harel et al. | |
| 2009/0118797 A1 | 5/2009 | Kliger et al. | |
| 2009/0131993 A1 | 5/2009 | Rousso et al. | |
| 2009/0204063 A1 | 8/2009 | Policker et al. | |
| 2009/0281449 A1 | 11/2009 | Thrower et al. | |
| 2010/0228105 A1 | 9/2010 | Policker et al. | |
| 2010/0305468 A1 | 12/2010 | Policker et al. | |
| 2010/0324644 A1 | 12/2010 | Levi et al. | |

FOREIGN PATENT DOCUMENTS

| | | |
|---|---|---|
| EP | 0421780 | 4/1991 |
| EP | 0727241 | 8/1996 |
| EP | 0996482 | 5/2000 |
| EP | 1447632 | 8/2004 |
| EP | 1515102 | 3/2005 |
| GB | 1394171 | 5/1975 |
| GB | 2033587 | 5/1980 |
| JP | 06-193884 | 7/1994 |
| JP | 06-310268 | 11/1994 |
| JP | 07-508662 | 9/1995 |
| JP | 08-064359 | 3/1996 |
| JP | 08-243176 | 9/1996 |
| JP | 09-229372 | 9/1997 |
| JP | 2001-086967 | 4/2001 |
| RU | 0386634 | 10/1973 |
| RU | 0553977 | 5/1977 |
| RU | 0709078 | 1/1980 |
| RU | 0831131 | 5/1981 |
| RU | 1039506 | 9/1983 |
| RU | 1147408 | 3/1985 |
| RU | 2014844 | 6/1994 |

| | | |
|---|---|---|
| RU | 1827793 | 5/1995 |
| RU | 2055606 | 3/1996 |
| RU | 2075980 | 3/1997 |
| RU | 2077273 | 4/1997 |
| RU | 2078547 | 5/1997 |
| RU | 2260451 | 10/2001 |
| WO | WO 93/02743 | 2/1993 |
| WO | WO 93/18820 | 9/1993 |
| WO | WO 94/01172 | 1/1994 |
| WO | WO 94/17855 | 8/1994 |
| WO | WO 96/10358 | 4/1996 |
| WO | WO 97/25098 | 7/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 98/57701 | 12/1998 |
| WO | WO 99/03533 | 1/1999 |
| WO | WO 99/24110 | 5/1999 |
| WO | WO 00/16741 | 3/2000 |
| WO | WO 00/53257 | 9/2000 |
| WO | WO 00/74773 | 12/2000 |
| WO | WO 01/10375 | 2/2001 |
| WO | WO 01/52931 | 7/2001 |
| WO | WO 01/66183 | 9/2001 |
| WO | WO 01/91854 | 12/2001 |
| WO | WO 01/93950 | 12/2001 |
| WO | WO 01/93951 | 12/2001 |
| WO | WO 02/23953 | 3/2002 |
| WO | WO 02/053093 | 7/2002 |
| WO | WO 02/082968 | 10/2002 |
| WO | WO 03/045493 | 6/2003 |
| WO | WO 2004/021858 | 3/2004 |
| WO | WO 2004/080533 | 9/2004 |
| WO | WO 2004/112563 | 12/2004 |
| WO | WO 2004/112883 | 12/2004 |
| WO | WO 2005/007232 | 1/2005 |
| WO | WO 2005/023081 | 3/2005 |
| WO | WO 2005/087310 | 9/2005 |
| WO | WO 2005/106333 | 11/2005 |
| WO | WO 2006/018851 | 2/2006 |
| WO | WO 2006/073671 | 7/2006 |
| WO | WO 2006/087712 | 8/2006 |
| WO | WO 2006/087717 | 8/2006 |
| WO | WO 2006/097934 | 9/2006 |
| WO | WO 2006/102626 | 9/2006 |
| WO | WO 2006/129321 | 9/2006 |
| WO | WO 2006/119467 | 11/2006 |
| WO | WO 2007/080595 | 7/2007 |
| WO | WO 2007/096877 | 8/2007 |
| WO | WO 2007/096878 | 8/2007 |
| WO | WO 2008/007368 | 1/2008 |
| WO | WO 2008/117296 | 10/2008 |
| WO | WO 2008/139463 | 11/2008 |
| WO | WO 2011/092710 | 8/2011 |
| ZA | 97/06341 | 2/1998 |

OTHER PUBLICATIONS

Pokrovsky et al. Physiology of Man, 1: 82-83, 94, 2: 42, 54.
Saveliev et al. Guidebook on Clinical Endoscopy, p. 21, 35, Extract.
Shmit et al. Physiology of Man, 1: 78, 1996.
Shuba et al. Physiology of Vessel Smooth Muscles, p.11-15, 142, 1988.
Van Riper et al. "Electrical Field Stimulation—Mediated Relaxation of A Rabbit Middle Cerebral Artery. Evidence of A Cholinergic Endothelium-Dependent Component", Circulation Research, 70: 1104-1112, 1992.
Zhou et al. "Prevention of Action Potentials During Extracellular Electrical Stimulation of Long Duration", Journal of Cardiovascular & Electrophysiology, 8(7): 779-789, 1997. Abstract.
Park et al. "Significant Cholinergic Role in Secretin-Stimulated Exocrine Secretion in Isolated Rat Pancreas", American Journal of Physiology, AJP—Gastrointestinal and Liver Physiology, 274(2): G413-G418, Feb. 1998.
Singh et al. "Effects of Islet Hormones on Nerve-Mediated and Acetylcholine-Evoked Secretory Responses in the Isolated Pancreas of Normal and Diabetic Rats", International Journal of Molecular Medicine, 1(3): 627-634, Mar. 1998. Abstract.
Antoni et al. "Polarization Effects of Sinusoidal 50-Cycle Alternating Current on Membrane Potential of Mammalian Cardiac Fibres", Pfl?gers Archiv European Journal of Physiology, 314(4): 274-291, 1970. Abstract.
Holst et al. "Nervous Contril of Pancreatic Endocrine Secretion in Pigs. I. Insulin and Glucagon Responses to Electrical Stimulation of the Vagus Nerves", Acta Physiologica Scandinavica, 111(1): Jan. 1-7, 1981. Abstract.
Holst et al. "Nervous Control of Pancreatic Endocrine Secretion in Pigs. II. The Effect of Pharmacological Blocking Agents on the Response to Vagal Stimulation", Acta Physiologica Scandinavica, 111(1): Jan. 9-14, 1981. Abstract.
Official Action Dated Feb. 23, 2010 From the US Patent and Trademark Office Re.: U.S. Appl. No. 11/932,963.
Response Dated Jan. 6, 2010 to Official Action of Jun. 26, 2009 From the US Patent and Trademark Office Re.: U.S. Appl. No. 11/932,812.
Antoni et al. "Polarization Effects of Sinusoidal 50-Cycle Alternating Current on Membrane Potential of Mammalian Cardiac Fibres", Pflügers Archiv European Journal of Physiology, 314(4): 274-291, 1970. Abstract.
Office Action Dated Nov. 29, 2004 From the Israeli Patent Office Re.: Application No. 133902.
Communication Pursuant to Article 94(3) EPC Dated Mar. 11, 2008 From the European Patent Office Re.: Application No. 06127216.7.
Communication Under Rule 71(3) EPC Dated Oct. 7, 2008 From the European Patent Office Re.: Application No. 06127216.7.
Notice of Reason for Rejection Dated Jun. 12, 2007 From the Japanese Patent Office Re.: Application No. 2000-502823.
Notice of Reasons for Rejection Dated Oct. 3, 2006 From the Japanese Patent Office Re.: Application No. 2000-502823.
Official Action Dated Dec. 11, 2009 From the US Patent and Trademark Office Re.: U.S. Appl. No. 11/932,881.
Official Action Dated Apr. 16, 2010 From the US Patent and Trademark Office Re.: U.S. Appl. No. 11/566,775.
Official Action Dated Jun. 28, 2010 From the US Patent and Trademark Office Re.: U.S. Appl. No. 11/932,963.
Requisition by the Examiner Dated Sep. 5, 2008 From the Canadian Intellectual Property Office Re.: Application No. 2,296,632.
Requisition by the Examiner Dated Jul. 14, 2004 From the Canadian Intellectual Property Office Re.: Application No. 2,296,632.
Requisition by the Examiner Dated Nov. 23, 2006 From the Canadian Intellectual Property Office Re.: Application No. 2,296,632.
Response Dated Jan. 5, 2010 to Official Action of Oct. 8, 2009 From the US Patent and Trademark Office Re. U.S. Appl. No. 11/566,775.
Response Dated Apr. 12, 2010 to Official Action of Dec. 11, 2009 From the US Patent and Trademark Office Re.: U.S. Appl. No. 11/932,881.
Response Dated Apr. 23, 2010 to Official Action of Feb. 23, 2010 From the US Patent and Trademark Office Re.: U.S. Appl. No. 11/932,963.
Notice of Allowance Dated Apr. 19, 2010 From the US Patent and Trademark Office Re.: U.S. Appl. No. 11/932,812.
Official Action Dated Jun. 26, 2009 From the US Patent and Trademark Office Re.: U.S. Appl. No. 11/932,812.
Response Dated May 10, 2011 to Notice of Allowance of Feb. 15, 2011 From the US Patent and Trademark Office Re.: U.S. Appl. No. 11/932,963.
Response Dated Nov. 29, 2010 to Official Action of Jun. 28, 2010 From the US Patent and Trademark Office Re.: U.S. Appl. No. 11/932,963.
Notice of Allowance Dated Feb. 15, 2011 From the US Patent and Trademark Office Re.: U.S. Appl. No. 11/932,963.

* cited by examiner

NT Signal

Force

NT Signal

Force

NT Signal

Force 300 mg 1 min

SMOOTH MUSCLE CONTROLLER FOR CONTROLLING THE LEVEL OF A CHEMICAL IN THE BLOOD STREAM

CROSS-REFERENCE TO PRIOR APPLICATIONS

This application is a divisional of U.S. patent application Ser. No. 10/282,968, filed Oct. 29, 2002, now U.S. Pat. No. 7,221,978 which is in turn a divisional of U.S. patent application Ser. No. 09/481,253, filed Jan. 11, 2000, now U.S. Pat. No. 6,571,127, which in turn is a continuation of PCT Application No. PCT/IL97/00243, filed Jul. 16, 1997, each of which is incorporated herein by reference.

FIELD OF THE INVENTION

The present invention is related to the field of controlling mechanical and/or electrical activity of smooth muscle by applying electrical fields to the muscle.

BACKGROUND OF THE INVENTION

In many body tissues, activity of individual cells, especially contraction, is initiated by changes in trans-membrane potentials. These types of tissue are also called excitable tissue, since when they are excited by an electrical signal, they react by activation. Some examples of excitable tissue include: cardiac muscle, skeletal muscle, smooth muscle and neural tissue. In many cases, the activity of large numbers of such excitable tissue cells is synchronized by propagating electrical activation signals. An activation signal is an electrical signal which, when it reaches an excitable cell, causes it to depolarize and perform its activity. In addition, the depolarization creates a new propagating activation signal which then continues to propagate towards the next un-activated cell. In most excitable tissue, the cell is refractory after a depolarization, such that the activation signal cannot immediately travel backwards.

The gastrointestinal (GI) tract is an example of a major physiological system in which many activities are coordinated by propagating electrical activation signals. The GI tract comprise a stomach, a small intestine and a large intestine. In a typical digestive process, food is chewed in the mouth and enters the stomach for digestion. The food is periodically passed to the antrum for grinding down and then passed back to the stomach. After a period of time, the pyloric sphincter opens and the food is passed to the small intestine. In the small intestine the food is churned and passed forward by a rhythmic motion of the intestines, until it reaches the large intestine. A one way sphincter allows movement only from the small intestine to the large intestine. Once in the large intestine, the food is further churned and compacted by motions of the large intestines. These motions also advance the digested food, now feces, to a pair of outlet sphincters, which mark the end of the GI tract.

The GI tract is mostly composed of smooth muscle, which, when depolarized, contracts. All of the above described movements of the GI tract are synchronized by propagating activation signals. As can be appreciated, in many cases, these electrical signals are not properly activated and/or responded to, resulting in disease. In one example, an ulcer causes inflammation of GI tissue. The inflamed tissue may generate spurious activation signals, which can cause the stomach to contract in a chaotic manner. The inflamed tissue may also affect the activation profile of the stomach by not conducting activation signals or by having a different conduction velocity than healthy tissue.

Pacing the GI tract is well known in the art, for example as shown in U.S. Pat. Nos. 5,292,344 and 5,540,730, the disclosures of which are incorporated herein by reference. The '730 patent describes both increasing and decreasing the excitability of the GI tract by stimulating different portions of the vagus nerve. The '344 Patent describes a pacemaker which directly stimulates portions of the GI tract. Electrical stimulation of the GI tract is also known to be used for stimulating the GI tract of patients suffering from post operative damping syndrome, as evidenced by SU 1039506, the disclosure of which is incorporated herein by reference.

The uterus also comprises smooth muscle, which contracts in response to electrical activation signals. "Uterine Electromyography: A Critical Review" by D. Devedeux, et al., *Am. J. Obstet Gynecol* 1993; 169:1636-53, the disclosure of which is incorporated herein by reference, describes the different types of uterine muscle and electrical signals generated by such muscles. An important finding which is described therein is that electrical activity in the uterus appears to be uncorrelated prior to labor, but when labor is established, the contractions and the electrical activity associated to them become highly synchronized.

In current medical practice, labor can be delayed by administering certain drugs. However, the operation of these drugs is somewhat uncertain. In addition, labor can be induced using other drugs, such as Oxytocin. Unfortunately, the dosage of Oxytocin which is required cannot be known in advance and overdoses of the drug can result in over-contraction which can mechanically damage the fetus and/or the mother.

SU 709078, the disclosure of which is incorporated herein by reference, describes stimulating the uterus after labor using an externally applied electrical current, to increase the contractions and aid in the expulsion of the afterbirth and reduce bleeding by rapidly shrinking the uterus.

The use of locally applied electrical fields for reducing pain is well known in the art. "Electrical Field Stimulation-Mediated Relaxation of a Rabbit Middle Cerebral Artery", D. A. Van Ripper and J. A. Bevan, *Circulatory Research* 1992; 70:1104-1112, the disclosure of which is incorporated herein by reference, describes causing the relaxation of an artery by applying an electric field. U.S. Pat. No. 4,537,195, the disclosure of which is incorporated herein by reference, describes treatment of pain using TENS (Transcutaneous Electrical Nerve stimulation), for treatment of headaches. It is hypothesized in this patent that the electrical stimulation prevents the constriction of arteries by stimulation of the muscle in the walls of the arteries, thereby preventing the dilation of capillaries, which dilation is a cause of headaches.

SU 1147408, the disclosure of which is incorporated herein by reference, describes a method of changing the distribution of blood flow in and about the liver, by applying electrical fields to arteries, varying the frequency of the field in synchrony with the cardiac rhythm.

U.S. Pat. No. 5,447,526, the disclosure of which is incorporated herein by reference, describes a transcutaneous electrical smooth muscle controller for inhibiting or decreasing the contraction of smooth muscle, especially uterine muscle. The controller, which is applied to the outside of the abdomen may also sense muscle contractions and effect inhibitory or stimulatory pulses unto the uterus as a whole, depending on the medical application, in response to sensed contractions.

SUMMARY OF THE INVENTION

It is an object of some aspects of the present invention to provide a method of directly and locally controlling the contraction and/or force of contraction of smooth muscles. Such control is especially employed, in particular preferred embodiments of the invention, in the gastrointestinal (GI) tract, the uterus, the bladder, endocrine glands, the gall bladder and blood vessels.

The inventors have found that the force of contraction of a smooth muscle can be both increased and decreased by a judicial application of a non-excitatory electric field. A non-excitatory electric field is an electric field which does not induce a propagating action potential in the smooth muscle. Such a non-excitatory electric field does, however, modify the reaction of the smooth muscle to an excitatory field. The inventors have also found that it is possible to desensitize smooth muscle to an activation signal, thereby the desensitized smooth muscle does not respond to an activation signal and also does not propagate the activation signal. Shortly after the field is removed, its effects are undone. It should be appreciated that many smooth muscles are characterized by multiple layers of fibers, the fibers in each layer having a preferred orientation. In a preferred embodiment of the invention, individual layers are selectively controlled by applying the electric field to be substantially parallel to the fiber orientation (in which case the field is highly effective). When a lesser degree of interaction between the muscle layer and the field is desired, the field is preferably applied perpendicular to the muscle fibers.

It is an object of some embodiments of the present invention to provide a method of more precisely controlling the GI tract than is possible using drugs and/or single or multi-site pacing. In a preferred embodiment of the present invention, the force of contraction of a portion of the GI tract is increased, such as to compensated for weakened contraction and/or to advance an otherwise stuck bolus. Alternatively or additionally, the force of contraction may be reduced, such as to treat a patient with overly sensitive intestines. Alternatively or additionally, a section of the intestines may be desensitized or blocked from electrical activation signals in order to promote the healing of a lesion in the section. Reducing or blocking contraction is also useful in treating acute diarrhea and to stop leakage from a stoma, when such leakage is undesired. Additionally or alternatively, the activation profile of the GI tract, which normally includes a forward moving wave and a returning wave, is changed, for example, by blocking the returning wave (the reflux), so as to increase the motility of the intestines. Blocking the returning wave may be performed by desensitizing one or more segments of the intestines after the forward wave has passed, so that the returning wave will be stopped at the desensitized segment. Alternatively, the entire length of the intestines is desensitized for the duration of the returning wave. After the returning wave is stopped, the desensitizing field is preferably stopped so as to allow the forward wave to properly propagate. The forward and returning waves can be detected either by their mechanical activity or, more preferably, by their electrical activity.

In a particular preferred embodiment of the present invention, the tension of the lower end of the colon is reduced so as to improve local blood supply and aid in the healing of hemorrhoids and anal fissures. It has recently been suggested that much of the pain associated with hemorrhoids is caused by ischemia of the tissue, which in turn, is caused by abnormally increased tension of the lower colon. Such tension has been hereunto been treated using topically applied drugs, such as nitroglycerin.

An endoscope, in accordance with another preferred embodiment of the present invention, locally controls the activity of the intestines so as to cause the smooth muscle to advance and/or retreat the endoscope. Alternatively or additionally, local electrical desensitization is used as a replacement and/or in addition to relaxation of the bowels using drugs.

Although some of the embodiments of the present invention have been described with respect to an endoscope or a colonoscope, these embodiments of the invention should be understood to apply to invasive probes in general and to endoscopes, colonoscopes, hysteroscopes and rectoscopes, in particular.

It is an object of another preferred embodiment of the present invention to provide a method of more precisely controlling labor, including, delaying and/or advancing the onset of labor, increasing or decreasing the length of labor and/or stopping labor from proceeding after it has started or when it is still in the pre-labor stages. Stopping labor is especially important for treating cases of pre-term onset of labor. Such control is exerted, in accordance with a preferred embodiment of the invention, by reducing the contractility of the uterine muscles, increasing their contractility or by desensitizing them so that synchronized contractions cannot occur. It is hypothesized that labor is a self-feeding process, where increased forces of contraction generate even stronger forces of contraction in the next contraction cycle. By damping the contraction force, such a feedback loop can be broken. In addition, when the uterus is desensitized, contractions cannot occur and labor is at least temporarily stopped, without significant danger to the fetus, as might be expected from drugs. Labor interrupted in this way can be rapidly restarted, without the problems associated which drug-terminated labor. In a preferred embodiment of the invention, spurious electrical activation signals arising from anomalous portions of the uterus, such as fibroid containing portions, which activation signals may cause premature labor, are reduced by local desensitizing and/or blocking of the uterine tissue.

It accordance with another preferred embodiment of the invention, menstruationally meditated contractions of the uterus (cramps) are treated by detecting such cramps and applying a desensitizing electrical field to the uterus to damp such cramps. Alternatively, such a desensitizing electric field may be applied during the time when such cramps may be expected to occur.

An object of another preferred embodiment of the present invention is to control the contractility of the bladder. In one preferred embodiment of the invention, the bladder is desensitized such that it does not spontaneously contract when such contraction is undesirable. Preferably, an apparatus for controlling the bladder in accordance with a preferred embodiment of the invention, includes a feedback mechanism, which stops its activity when the bladder becomes over full. In an additional or alternative embodiment of the invention, the force of contraction of the bladder is increased during urination. In a preferred embodiment of the invention, the force of contraction of the bladder is increased in patients having bladder hypertrophy, so that the bladder will gradually shrink. Such treatment is preferably combined with drug treatment and/or an implantation of a stent, which treatments may be used to reduce blockage of the urethra.

In accordance with another preferred embodiment of the invention, the output rate of endocrine or neuro-endocrine glands is controlled, preferably reduced, by applying a desensitizing electric field. In a preferred embodiment of the invention, a desensitizing electric field is applied to the beta islet cells of the pancreas, so as to reduce insulin generation in patients suffering from hyper-insulinemia levels. Preferably, such control is applied without measuring the electrical activity of the beta islet cells. Alternatively or additionally, such control is applied while monitoring the blood glucose level. The desensitizing field is preferably a locally applied DC field, whose polarity is switched at a very low frequency, such as once an hour, so as to avoid polarization of the electrodes and/or damage to the tissue.

Another aspect of the present invention relates to treating vascular spasm, angina pectoris and/or abnormal blood pressure, by electrically controlling large blood vessels in the body. In accordance with a preferred embodiment of the invention, large veins, such as the abdominal veins are relaxed by applying a local inhibitory electric field to them. Alternatively or additionally, large arteries, such as the aorta, are relaxed by applying a local inhibitory electric field to them. Alternatively or additionally, excitatory fields are applied to the arteries and/or veins so as to constrict them. As can be appreciated, changing the volume of the arteries and veins can directly affect a patient's blood pressure and/or cardiovascular performance. In addition, relaxing the veins reduces the preload to the heart, which can stop an episode of ischemia, e.g., angina pectoris. Further, relaxing the aorta is useful in cases of vascular spasm, which, in many cases, is the cause of angina pectoris.

The relaxing electrical field is preferably applied to the blood vessels in spasm, which, in some cases, may be coronary blood vessels. Electrically induced relaxation of blood vessels may be used instead of or in addition to pharmaceuticals. Further, forced relaxation of arteries and veins is useful for treating an acute ischemic event. Typically, the ischemic event causes increased heart rate which further strains ischemic cardiac tissue. By reducing the preload and/or the afterload of the heart, the cardiac demand is reduced, which reduces the oxygen demand of the ischemic tissues and/or allows better perfusion of the ischemic tissues. Additionally or alternatively, the diastole may be extended to aid the perfusion of the cardiac muscle. Extending the diastole may be achieved, for example, by desensitizing at least a portion of the heart, using techniques, such as described in PCT IL97/00012, "Electrical Muscle Controller", filed on Jan. 8, 1997, the disclosure of which is incorporated herein by reference.

There is therefore provided for, in accordance with a preferred embodiment of the invention, a method of promoting the healing of a lesion in a smooth muscle, comprising:

selecting a smooth muscle portion having a lesion; and applying a non-excitatory electric field to the portion, which field reduces the mechanical activity at the portion.

Preferably, applying an electric field comprises desensitizing the smooth muscle portion. Alternatively or additionally, applying an electric field comprises blocking the electrical activity of smooth muscle surrounding the lesion.

Preferably, the lesion is an ischemic portion of the muscle. Alternatively or additionally, the lesion is a sutured portion of the muscle.

Preferably, reducing the mechanical activity comprises inhibiting mechanical activity at the location.

In a preferred embodiment of the invention, the smooth muscle portion is part of a gastrointestinal (GI) tract.

There is also provided in accordance with a preferred with a preferred embodiment of the invention, a method of treating diarrhea, comprising:

selecting a portion of irritated intestine; and applying an electric field to the portion, which field reduces the mechanical activity at the portion.

There is also provided in accordance with a preferred embodiment of the invention, a method of treating obesity, comprising:

selecting at least a portion of a stomach; and applying an electric field to the portion, which field delays or prevents the emptying of the stomach.

There is also provided in accordance with a preferred embodiment of the invention, a method of treating nausea, comprising, selecting at least a portion of a stomach; and applying an electric field to the portion, which field reduces the mechanical activity of the stomach.

There is also provided in accordance with a preferred embodiment of the invention, a method of controlling emptying of a stoma, comprising:

applying an electric field to an exit portion of the stoma, which field reduces the motility of the end portion; and removing said field when emptying of the stoma is desired.

Preferably, the method further comprises applying a second electric field to the exit portion, which second field increases the motility of the stoma, when emptying of the stoma is desired. The second field may be an excitatory field. Additionally or alternatively, the second field is one which increases the force of contraction.

There is also provided in accordance with a preferred embodiment of the invention, a method of treating a hemorrhoid, comprising:

providing a patient having a colon; and applying an electric field to a portion of the colon, which field relaxes at least a portion of the colon, near an exit therefrom.

Preferably, the hemorrhoid is not situated at said portion of the colon. Alternatively or additionally, the method comprises:

measuring a tension in the portion of the colon, wherein applying an electric field comprises applying an electric field when the measured tension is above a predetermined amount.

In a preferred embodiment of the invention, in a method a described above, applying an electric field comprises applying the electric field at a delay after a local activation time.

There is also provided in accordance with a preferred embodiment of the invention, a method of increasing the motility of a GI tract, comprising:

selecting a portion of the GI tract; and applying a non-excitatory electric field to the portion, which field increases the force of contraction at the portion.

Preferably the method includes applying a second electric field to a second portion of the GI tract, downstream from said portion, which second electric field decreases the force of contraction at the second portion.

There is also provided in accordance with a preferred embodiment of the invention, a method of increasing the motility of a GI tract, comprising:

determining a timing of a returning wave in the GI tract; and applying an electric field to at least a portion of the GI tract, which electric field reduces the response of the GI tract to the returning wave.

Preferably, determining a timing comprises detecting a forward wave and wherein applying an electric field comprises applying an electric field only at times where it does not substantially interfere with the forward wave.

Alternatively or additionally, determining a timing comprises detecting a returning wave and wherein applying an electric field comprises applying an electric field only at times where it substantially interfere with the returning wave.

Alternatively or additionally, applying an electric field comprises applying an electric field which inhibits the propagation of an activation signal, which activation signal synchronizes the returning wave.

Alternatively or additionally, applying an electric field comprises applying an electric field which reduces the force of contraction in at least a portion of the GI tract.

There is also provided in accordance with a preferred embodiment of the invention, a method of selectively exciting only a layer of muscle in a smooth muscle having a plurality of muscle layers, each with a different fiber orientation, comprising:

applying an inhibitory electrical field, parallel to the a fiber orientation of a first layer of muscle, to the muscle; and applying an excitatory electric field to the muscle, which electrical field excites a second layer of the muscle.

There is also provided in accordance with a preferred embodiment of the invention, a method of selectively increasing the force of contraction of only a layer of muscle in a smooth muscle having a plurality of muscle layers, each with a different fiber orientation, comprising:

applying an inhibitory electrical field, parallel to the a fiber orientation of a first layer of muscle, to the muscle; and applying a second electric field to the muscle, which second electric field is oriented parallel to the fiber orientation of a second layer of muscle and which second field increases the force of contraction in the second layer of muscle.

There is also provided in accordance with a preferred embodiment of the invention, a method of multi-point pacing for a smooth muscle, comprising:

applying excitatory electric fields at a plurality of locations on said muscle; and applying at least one inhibitory electric field at a second plurality of locations, situated among said plurality of locations, wherein said inhibitory electric field prevents the propagation of an activation signal between said first plurality of paced locations.

There is also provided in accordance with a preferred embodiment of the invention, apparatus for controlling at least the local activity of a portion of an in vivo smooth muscle, comprising:

a plurality of electrodes, adapted to be in contact with a portion of smooth muscle to be controlled; and a controller which electrifies said electrodes with an electrical field which does not generate a propagating action potential in the smooth muscle, which electrical field modifies the reaction of the smooth muscle to an activation signal.

Preferably, the apparatus includes an electrical activity sensor which detects electrical activity at the portion and wherein said controller electrifies said electrodes responsive to signals from said sensor. Preferably, the controller electrifies each of said electrodes is responsive to its local electrical activity. Additionally or alternatively, the electrical activity sensor senses electrical activity through ones of said plurality of electrodes.

Alternatively or additionally, the apparatus includes an impedance sensor, which senses at least one impedance between selected ones of said plurality of electrodes.

Alternatively or additionally, the apparatus includes a force transducer which detects mechanical activity at the portion and wherein said controller electrifies said electrodes responsive to signals from said sensor. Preferably, said controller applies an inhibitory electric field to the muscle, when said mechanical activity is above a certain threshold. Alternatively or additionally, the electrification at each of said electrodes is responsive to its local mechanical activity.

Alternatively or additionally, the non-excitatory field inhibits mechanical activity at the portion. Alternatively or additionally, the non-excitatory field reduces the force of contraction at the portion. Alternatively or additionally, the non-excitatory field increases the force of contraction at the portion. In a preferred embodiment of the invention, the controller electrifies at least one of said electrodes with an excitatory electric field.

In a preferred embodiment of the invention, the plurality of electrodes are arranged in a two-dimensional matrix.

Alternatively or additionally, the controller selectively electrifies ones of said plurality of electrodes to selectively generate one of two perpendicular electric fields.

In a preferred embodiment of the invention, the controller is adapted to be implanted inside a stomach and attached to the stomach wall.

Alternatively or additionally, the apparatus is adapted to be implanted inside a uterus and attached to the uterus wall.

Alternatively or additionally, the apparatus is adapted to be implanted inside the body and outside a portion of the GI tract.

Alternatively or additionally, the apparatus is adapted to be implanted inside the body and outside a uterus.

In a preferred embodiment of the invention, where the controller is adapted for a uterus, the controller determines a frequency of contractions in the uterus and wherein said controller electrifies said electrodes responsive to said determined frequency.

Preferably, the electrodes comprise elastic leads.

In a preferred embodiment of the invention, the electrodes are attached to a plurality of remote regions of said uterus.

In a preferred embodiment of the invention, the controller senses and inhibits mechanical activity in substantially the entire uterus. Alternatively or additionally, the controller increases the force of contraction in substantially the entire uterus.

In a preferred embodiment of the invention, the controller is in a capsule adapted to be inserted into a rectum or into a vagina.

Alternatively or additionally, the electrodes are adapted to be implanted inside the body while said controller is adapted to be situated outside the body. Preferably, the electrodes are adapted to be disconnected from said smooth muscle from outside the body.

There is also provided in accordance with a preferred embodiment of the invention, an anastomosis button comprising:

a sleeve portion for joining two portions of a GI tract;

at least two electrodes adapted to be in electrical contact with the GI tract, at either side of the button; and a controller which electrifies the electrodes to reduce the force of contraction in the GI tract near the button.

Preferably, the controller transmits a pacing signal from the GI tract on one side of the button to the GI tract on the other side of the button.

Alternatively or additionally, reducing the force comprises inhibiting electrical activity of the GI tract at the button.

There is also provided in accordance with a preferred embodiment of the invention, apparatus for inhibiting a returning wave in an intestine, comprises:

at least one electrode for applying an inhibiting electric field to a portion of the intestine;

a sensor which senses the propagation of waves in the intestine; and a controller which electrifies said electrode responsive to a sensed propagating wave.

Preferably, the sensor detects the returning wave.

There is also provided in accordance with a preferred embodiment of the invention, apparatus for advancing a bolus comprising:

at least one first electrode, for applying an electrical field to a first portion of the GI tract adjacent said bolus;

at least one second electrode, for applying an electric field to a second portion of the GI tract downstream from said bolus; and a controller which electrifies the at least one first electrode with a non-excitatory field which increases the force of contraction at the first portion and which electrifies the at least one second electrode with a non-excitatory electric field which relaxes the muscle at the second portion.

Preferably, the apparatus comprises an impedance sensor for detecting the existence of a bolus at the first portion of the GI tract.

There is also provided in accordance with a preferred embodiment of the invention, a method of aiding the examination of a GI tract, comprising:

providing an elongated probe, having a tip, inside a portion of a GI tract; and applying a non-excitatory electric field to the portion of the GI tract adjacent the tip of the probe, which electric field is operative to relax the portion of the GI tract.

Preferably, the method includes inflating the portion of the GI tract after applying said field.

Preferably, the portion of the GI tract is a portion adjacent a bile duct.

There is also provided in accordance with a preferred embodiment of the invention, a method of advancing an elongated probe having a tip and inserted in a portion of the GI tract, comprising:

applying a first electric field at the tip, which field constricts the portion of GI tract to grasp the probe; and applying a second electric field to a second portion of the GI tract adjacent a portion of the probe distal from the tip, which electric field causes the elongation of the second portion of the GI tract.

Preferably, the method includes applying a third electrical field to a third portion of the GI tract, adjacent portions of the probe distal from the tip, which electrical field relaxes the third portion of the GI tract so that it does not constrict around the probe.

Alternatively or additionally, the method includes applying an inhibitory electric field to block the propagation of activation signals between the first portion and other portions of the GI tract.

There is also provided in accordance with a preferred embodiment of the invention, a method of advancing an elongated probe, comprising:

providing an elongated probe, having a tip, inside a portion of a GI tract; and applying an excitatory electric field to the portion of the GI tract, which excitatory electric field causes the bowel to transport the probe in a desired direction.

Preferably, the excitatory field is selectively applied either at the tip or at a different location along the probe, distal from the tip, depending on the desired direction of transport.

Alternatively or additionally, the method includes applying an inhibitory electric field, to the portion, to block the propagation of activation signals between the portion and the rest of the GI tract.

In a preferred embodiment of the invention, the probe is an endoscope. Alternatively, the probe is a colonoscope.

There is also provided in accordance with a preferred embodiment of the invention, an elongated probe adapted for advancing in a GI tract, comprising:

an elongated body having a tip;

a plurality of electrodes disposed at least at the tip; and a controller which selectively electrifies the electrodes to produce non-excitatory electric fields which affect the contraction of smooth muscle.

Preferably, the probe includes a second plurality of electrodes distributed along at least a portion of the body of the probe.

Alternatively or additionally, the controller electrifies said first plurality of electrodes to cause said portion of GI tract to selectively advance or retreat said probe.

Alternatively or additionally, the controller electrifies ones of said first and said second pluralities of electrodes to inhibit the propagation of activation signals from the portion of the GI tract adjacent the tip of the probe to other portions of the GI tract.

There is also provided in accordance with a preferred embodiment of the invention, a method of controlling a uterus, comprising:

determining a portion of the uterus suspected of generating undesirable activation signals; and applying a local inhibitory electrical field, to the uterus muscle, around the suspected portion.

There is also provided in accordance with a preferred embodiment of the invention, a method of controlling a uterus, comprising:

determining a portion of the uterus suspected of generating undesirable activation signals; and applying a local desensitizing electrical field to the suspected portion.

There is also provided in accordance with a preferred embodiment of the invention, a method of controlling labor, comprising:

determining a local activation at a plurality of locations of a uterus; and applying a non-excitatory electric field, to each of the plurality of locations, at a time delay from said local activation time.

Preferably, the non-excitatory field increases the force of contraction at ones of said plurality of locations.

Alternatively or additionally, said non-excitatory field reduces the force of contraction at ones of said plurality of locations.

Alternatively or additionally, the non-excitatory field inhibits the conduction of propagating action potentials across the uterus.

In a preferred embodiment of the invention, the method includes implanting a plurality of electrodes at the plurality of locations. Preferably, the electrodes comprise encapsulated power sources. Alternatively or additionally, the implanting is performed during a cesarean section.

There is also provided in accordance with a preferred embodiment of the invention, a method of aiding birth, comprising applying a non-excitatory electrical field to a birth canal, which non-excitatory field relaxes the birth canal.

There is also provided in accordance with a preferred embodiment of the invention, a method of preventing premature birth, comprising applying a non-excitatory electrical field to a birth canal, which non-excitatory field increases the force of contraction in the birth canal.

There is also provided in accordance with a preferred embodiment of the invention, a method of treating cramps of the uterus, comprising:

detecting electrical or mechanical activity in at least one location of the uterus; and applying a non-excitatory electrical field at the at least one location.

There is also provided in accordance with a preferred embodiment of the invention, a method of treating cramps, comprising:

providing at least one electrode inside the uterus, which one electrode is in contact with at least a portion of the uterus, at at least one location thereof; and applying a non-excitatory electrical field to the portion.

In a preferred embodiment of the invention, the non-excitatory field inhibits the propagation of activation signals at the at least one location. Alternatively or additionally, non-excitatory field reduces the force of contraction at the at least one location.

There is also provided in accordance with a preferred embodiment of the invention, apparatus for controlling a smooth muscle, comprising a plurality of individual capsules, each capsule including at least one electrode and a power source which electrifies the electrode, which electrode applies a local non-excitatory field. Preferably, each of said capsules includes a sensor which measures local activity of the smooth muscle.

Alternatively or additionally, the capsules are operative to synchronize the electrification of their electrodes without the meditation of an external controller.

There is also provided in accordance with a preferred embodiment of the invention, apparatus for treating cramps, comprising:

a flexible body having an outside portion and adapted to snugly engage the inside of a uterus;

a plurality of electrodes disposed on the outside of said body; and a controller which electrifies said electrodes to generate a non-excitatory electrical field.

Preferably, the flexible body is inflatable. Alternatively or additionally, the apparatus includes a second electrode adapted to be placed outside the uterus.

There is also provided in accordance with a preferred embodiment of the invention, a method of controlling a circulatory system, including a heart, comprising:

providing electrodes adjacent a vein; and electrifying the electrodes to constrict the vein, such that the preload on the heart is increased.

There is also provided in accordance with a preferred embodiment of the invention, a method of controlling a circulatory system, including a heart, comprising:

providing electrodes adjacent a vein; and electrifying the electrodes to expand the vein, such that the preload on the heart is reduced.

There is also provided in accordance with a preferred embodiment of the invention, a method of controlling a circulatory system, including a heart, comprising:

providing electrodes adjacent an artery; and electrifying the electrodes to constrict the artery, such that the afterload on the heart is increased.

There is also provided in accordance with a preferred embodiment of the invention, a method of controlling a circulatory system, including a heart, comprising:

providing electrodes adjacent an artery; and electrifying the electrodes to expand the artery, such that the afterload on the heart is reduced.

There is also provided in accordance with a preferred embodiment of the invention, a method of controlling vascular spasm, in a circulatory system having a heart, comprising:

determining a vessel in spasm, which results in an abnormally constricted lumen; and applying a non-excitatory electric field to the vessel, which field causes the lumen to expand.

It should be appreciated that two or more of the above methods of controlling the circulatory system may also be practiced together.

In a preferred embodiment of the invention, the method includes applying a non-excitatory electric field to at least a portion of the heart.

There is also provided in accordance with a preferred embodiment of the invention, apparatus for controlling a circulatory system having a heart, comprising:

a plurality of electrodes disposed about at least one major blood vessel;

a blood pressure sensor which measures blood pressure; and a controller which electrifies the plurality of electrodes responsive to the measured blood pressure.

Preferably, the apparatus includes an external control which activates said controller.

Alternatively or additionally, the apparatus includes an ECG sensor which detects the cardiac rhythm. Alternatively or additionally, the controller relaxes said blood vessel to reduce the blood pressure. Alternatively or additionally, the controller contracts said blood vessel to increase the blood pressure.

There is also provided in accordance with a preferred embodiment of the invention, a method of controlling the output of a gland, comprising:

providing at least one electrode near the gland; and applying a non-excitatory electric field to the gland.

Preferably, the non-excitatory electric field inhibits the activity of hormone producing cells in the gland. Alternatively or additionally, the non-excitatory electric field is a substantially DC field. Preferably, the method includes periodically changing the polarity of the field. Preferably, one polarity is applied for a significantly larger portion of the time.

In a preferred embodiment of the invention, the gland is a pancreas. Preferably, the method includes monitoring a level of glucose in the blood, wherein applying said electric field comprises applying said field responsive to said monitored level.

There is also provided in accordance with a preferred embodiment of the invention, apparatus for controlling the output of a gland, comprising:

a sensor for measuring a level of a chemical in a blood stream;

at least one electrode adjacent said gland; and a controller which electrifies said electrode with a non-excitatory electric field, responsive to the measured level.

Preferably, the chemical is glucose. Alternatively or additionally, the apparatus is completely implantable.

There is also provided in accordance with a preferred embodiment of the invention, a method of controlling the activation profile of a smooth muscle organ, comprising:

determining a desired activation profile for the organ; and applying at least one non-excitatory field to a portion of the organ to modify its activation profile.

Preferably, the activation profile comprises a mechanical activation profile.

In a preferred embodiment of the invention, the method includes:

measuring a tension in the smooth muscle; and modifying the application of the non-excitatory field responsive to the measured tension.

Alternatively or additionally, the method includes:

measuring a pressure in the smooth muscle; and modifying the application of the non-excitatory field responsive to the measured pressure.

Alternatively or additionally, the method includes applying at least one excitatory electric field to the smooth muscle.

Alternatively or additionally, the method includes applying a non-excitatory field comprises applying an inhibitory electric field to the muscle.

Alternatively or additionally, applying a non-excitatory field comprises applying an electric field which reduces the force of contraction in the muscle.

Alternatively or additionally, applying a non-excitatory field comprises applying an electric field which increases the force of contraction in the muscle.

Preferably, the organ is a stomach. Alternatively or additionally, the organ is a small intestine. Alternatively or additionally, the organ is a large intestine. Alternatively or additionally, the organ is a uterus.

There is also provided in accordance with a preferred embodiment of the invention, apparatus for dictating a mechanical activation profile to a smooth muscle organ, comprising:

at least three electrodes, adapted to be distributed over the organ;

at least one sensor which senses local mechanical activity of the organ; and a controller which electrifies selected ones of said electrodes, responsive to the sensed local mechanical activity, to dictate a particular activation profile to the organ.

Preferably, the organ is a uterus and wherein the activation profile is a pattern of contraction during labor.

Although many embodiments of the present invention are described herein mainly as methods, it should be appreciated that the scope of the invention includes apparatus adapted to perform these methods. In particular, the scope of the invention includes programmable electric field generators which are programmed to supply an electric field in accordance with a preferred embodiment of the invention. In a preferred embodiment of the invention, programmable variables include, waveforms, amplitudes, frequencies, durations, delays, synchronization and response to locally measured parameters of muscle activity. It should be appreciated that the behavior of a muscle in one portion thereof can be modified by applying an electric field to a second portion thereof, for example, by inhibiting the propagation of an activation signal to the one portion or by changing the layout of forces acting on the one portion.

BRIEF DESCRIPTION OF THE DRAWINGS

The present invention will be more clearly understood from the following detailed description of the preferred embodiments of the invention, together with the accompanying figures, in which.

DETAILED DESCRIPTION OF THE PREFERRED EMBODIMENTS

Figure 1:
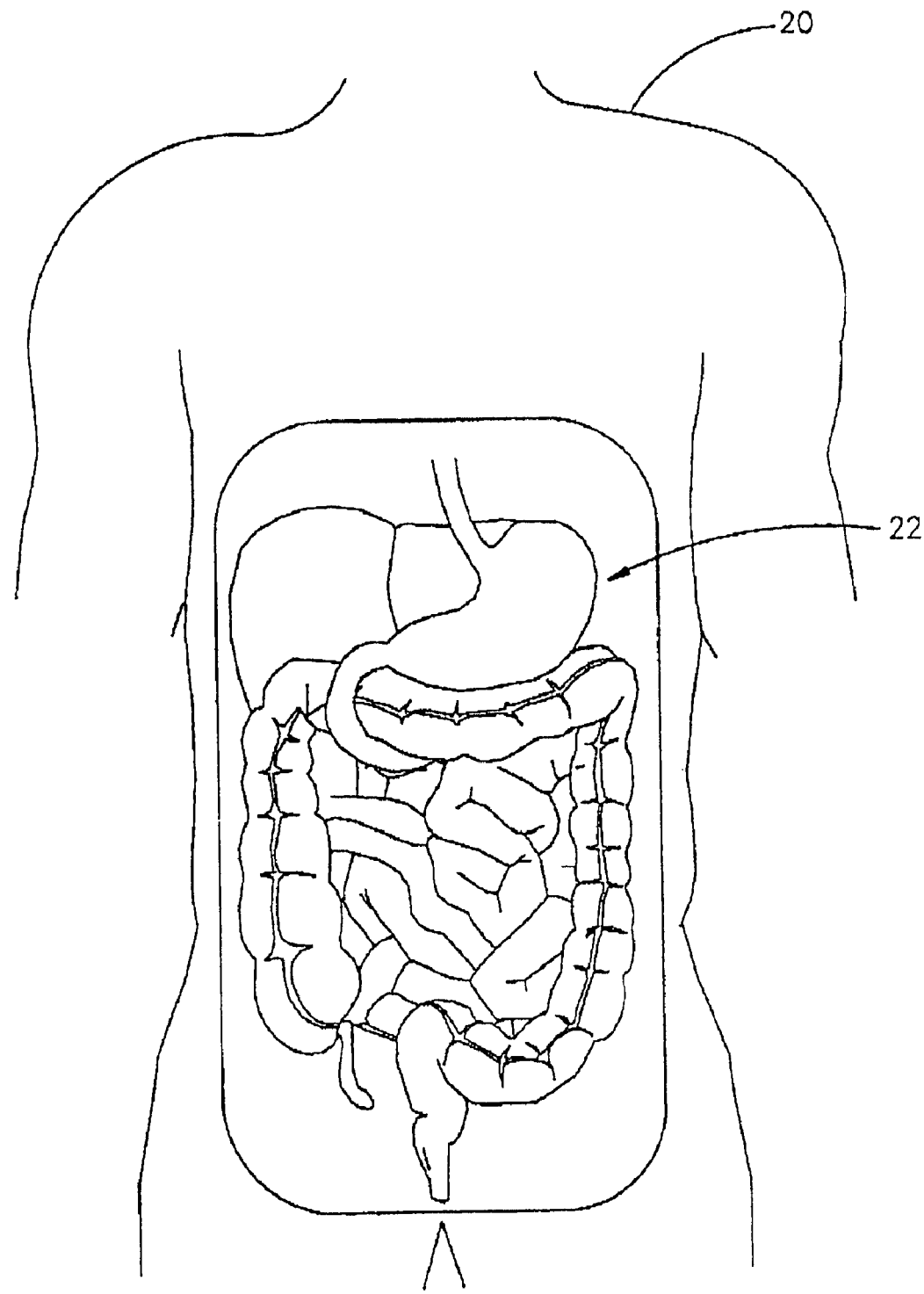
FIG. 1 is a schematic illustration of a gastrointestinal (GI) tract.

FIG. 1 is a schematic illustration of a gastrointestinal (GI) tract 22 of a patient 20. In accordance with a preferred embodiment of the invention, local control of the force of contraction and/or the sensitivity of portions of the GI tract to excitation is achieved by applying local, non-excitatory electric fields directly to the portion to be controlled. Although such non-excitatory electric fields do not create a propagating action potential in the controlled portion, the fields does modify the response of the portion to an artificial or naturally occurring activation signal, when it arrives. In particular, the inventors have found that it is possible to increase or to decrease the force of contraction of a portion of GI tract. In addition, it is possible to desensitize a muscle segment so that it has a reduced reaction or so it does not react at all to normal amplitudes of activation signals. This desensitization, while reversible, may be made to last a certain period of time after the removal of the controlling electric field.

Two particular waveforms of non-excitatory electric fields have been found to be beneficial. A first type is a substantially constant field (whose polarity may be occasionally switched to reduce ionic polarization effects). This field may be applied without any synchronization to the controlled muscle. However, the inventors have found it useful to stop the inhibiting field shortly before the activation signal is to arrive at the controlled muscle, so as to reduce the amplitude of activation signal required to excite the controlled muscle. A second type of non-excitatory field is a pulse which is applied in synchrony with the arrival of an activation signal. The pulse is applied either before, during the arrival of the signal or at a delay after its arrival (a long enough delay after activation is equivalent to applying the pulse before activation). The inventors believe that a non-excitatory electric field applied after the activation signal tends to increase the force of contraction of the controlled muscle, by increasing a plateau duration of the muscle contraction. It is hypothesized that a non-excitatory field applied at a greater delay after the arrival of the activation signal extends the refractory period (possibly by hyperpolarizing the muscle cells so that the activation signal does not cause a depolarization). As a result, at least some of the muscle cells do not respond to the activation signal and the force of contraction of the muscle is reduced. Thus, the stronger the non-excitatory signal, the more cells will be hyperpolarized and the lower will be the force of contraction. In an extreme case, none of the muscle cells will respond to the activation signal and the propagation thereof will be inhibited. It is also possible that the non-excitatory field directly reduces affects the force of contraction achieved by a single muscle fiber.

It should be noted that various embodiments of the present invention, as described herein, can be used in conjunction with drug therapies, with a synergistic interaction and/or to allow a reduced dose of drug to produce a desired effect and/or to allow increased dosages of drugs to be used, while limiting their adverse side effects using electrical control. In addition, such electrical control may be practiced together with electrical pacing of the GI tract, including multi-site pacing. In accordance with a preferred embodiment of the present invention, substantially any activation profile of the GI tract may be achieved by selectively pacing portions of the GI tract and creating desensitized regions between the paced portions, so that an activation signal does not propagate from one paced portion to the next. In addition, such electrical control may also be practiced in combination with electrical stimulation of a vagus nerve.

The term "electric field" has been used to described the non-excitatory field used to control a muscle. The terms "field" and "current pulse" are used interchangeably herein, since, in the body, both are generated when a voltage potential is created between two electrodes. In a preferred embodiment of the invention, the field is applied by maintaining a constant current between at least two electrodes. Alternatively, a voltage potential may be controlled instead of controlling the current.

Muscle tissue generally adapts to frequent and/or intense activation by increasing its mass. In a preferred embodiment of the invention, the pacing location is chosen to increase the strength of the muscle at the location. Preferably, the area around the location is desensitized so that the activation signal does not propagate to the rest of the GI tract. Alternatively or additionally, local muscle mass is increased by modifying the force of contraction at the location. Generally, a maximum force of contraction is desired, since it will generally cause the greatest increase in muscle mass.

Figure 2:
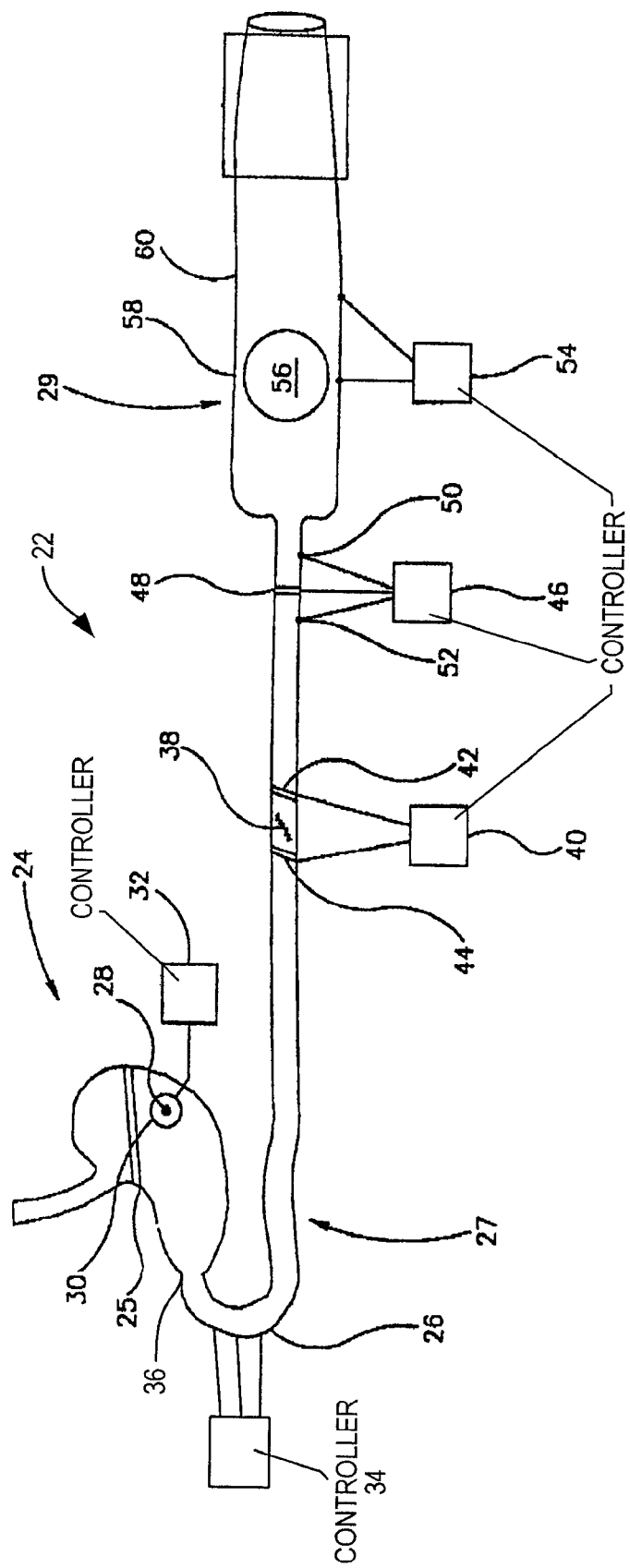
FIG. 2 is a schematic illustration of an unfolded GI tract, illustrating various preferred embodiments of the present invention.

FIG. 2 is a schematic drawing of GI tract 22, unfolded for illustrative purposes, for illustrating various preferred embodiments of the present invention. GI tract 22 includes a stomach 24, a duodenum 26, a small intestine 27 and a large intestine 29.

In accordance with a first preferred embodiment of the invention, a portion of the GI tract is desensitized and/or electrically isolated from activation signals. Isolation from electrical signals may be achieved by desensitizing tissue which surrounds the portion.

Ulcers cause inflammation of the GI tract tissue, which inflamed tissue may generate spurious activation signals. Alternatively, the inflamed tissue may exhibit a very low threshold of excitability. Both these abnormalities may cause arrhythmias in stomach 24. In a preferred embodiment of the invention, an ulcer 28 is prevented from generating abnormal electrical activity in stomach 24 by desensitizing the tissue surrounding the ulcer. Depending on the exact configuration, ulcer 28 itself may be desensitized. Alternatively or additionally, a non-excitatory field will be applied to regions surrounding ulcer 28 to fence it in by non-action potential propagating tissue.

The term fencing, as used herein refers to electrically isolating one segment of muscle from other segments, by inhibiting electrical activity in the tissue surrounding the one segment. Thus, an activation signal can neither enter nor leave the one segment. Alternatively to completely enclosing a segment, fences can be used to channel an activation signal along a desired path by creating fences on either side of the desired path. It should be noted that in channeling, it my be sufficient to significantly reduce the conduction velocity in the tissue where the fence is applied, since this will also modify the propagation vector of the activation front.

In a preferred embodiment of the invention, the tissue desensitization is accomplished by a controller 32, comprising an electrode 30, in contact with the tissue surrounding ulcer 28. Although in this embodiment, controller 32 is shown to be external to stomach 24 and either inside or outside the body, in an alternative preferred embodiment of the invention, controller 32 is implanted inside the stomach, preferably placed by the aid of an endoscope and/or an electrical activity mapping probe, and preferably fixed to the wall of stomach 24, such as by using clips.

In accordance with another preferred embodiment of the invention, the pacemaker portion of stomach 24, which is usually in the upper portion of stomach 24, is electrically isolated from other portions of the stomach. In FIG. 2 this is accomplished by applying a fence 25 in a band around stomach 24. Alternatively or additionally, the rest of stomach 24 may be desensitized. Alternatively or additionally, the pacemaker region itself may be desensitized to reduce its excitation rate. Desensitizing stomach 24 is useful for treating nausea, pregnancy related nausea, reflex vomiting and other stomach conditions characterized by undesirable activation of the stomach.

A particular example of a condition is in the treatment of obesity, treatable by stomach desensitization, where delaying emptying of stomach 24 leads to a "full" feeling and reduces the consumption of food by the patient. Desensitization of the stomach is preferably applied together with pacing of the stomach to achieve the desired activation. Alternatively or additionally, intestines 27 are also controlled in a like manner, especially by blocking electrical activation signals from stomach 24 from arriving at intestine 27, such as by applying a fence at duodenum 26 and/or at the antrum. In such examples, controller 32 is preferably controllable from outside the body, such as by using magnetic reed switches or using RF telemetry. Thus, controller 32 may activated and deactivated when the patient needs it. Alternatively or additionally, controller 32 includes sensors which sense various states of GI tract 22, including, the location of food in a portion thereof and local electrical activity. In such an embodiment, controller 32 can modify the activation profile of GI tract 22, responsive to the existence and position of food matter therein.

In accordance with another preferred embodiment of the invention, a portion of GI tract 22 is desensitized and/or fenced in to allow it to heal. FIG. 2 shows a sutured region 38, and a controller 40 which applies a pair of fences 42 and 44, so that region 38 will be electrically isolated and so that local muscle activity will not damage the suture. Region 38 might also comprise an area from which an ulcer has been recently removed. In a preferred embodiment of the invention, such a controller is incorporated in an anastomosis button, which is used to connect two segments of the intestine. Preferably, such an anastomosis button senses electrical activity at one side thereof and applied an excitatory signal at an opposite side thereof to assure a natural contraction of the intestines. Alternatively to completely inhibiting electrical activity at region 38 it may be desirable to intermittently allow local electrical and/or mechanical activity. Alternatively or additionally, the local force of contraction may be substantially reduced so as to reduce local stretching of the sutures. In a preferred embodiment of the invention, electrodes are implanted at the treated region during a laproscopic procedure (or an open-abdomen procedure). An inhibitory electrical field is applied until it is deemed unnecessary by medical opinion.

In a preferred embodiment of the invention, the electrodes are connected to an external muscle controller. Once the field is not necessary, the electrodes may be retracted, for example, using pull-out electrodes, as known in the art, for example, by twisting the electrodes or by releasing a suture which attaches the electrode to the muscle.

In a preferred embodiment of the invention, emptying of a stoma is inhibited by desensitizing the last few inches of the stoma, until such time as emptying thereof is desired. A controller for a stoma preferably includes electrodes implanted along the last few inches of the stoma for applying inhibitory or excitatory pulses. A stoma controller preferably also includes an external control button which allows the patient to choose between inhibiting the stoma, to stop exiting of solid wastes and stopping the inhibiting and/or stimulating the stoma, to allow travel of solid wastes along the stoma.

In a preferred embodiment of the invention, an electrical controller is used in lieu of a pharmaceutical to relax the bowels. One example which such a used is desirable is in spastic constipation, where a vicious cycle of tension-pain-constipation can be broken by relaxing the tension in the large intestines. A relaxing electrical field may be applied tanscutaneously, by implanted electrodes or may be applied using an inserted probe.

In another preferred embodiment of the invention, pains caused by ischemia of the intestines are reduced by reducing the contractility of the muscle at the diseased area, thereby reducing oxygen consumption and/or allowing better perfusion. Preferably, such a controller includes a pressure sensor and the controller is adjusted to reduce the force of contraction after a preset local force of contraction is reached.

In another preferred embodiment of the invention, acute diarrhea is treated by relaxing small intestine 27 and/or large intestine 29, so that they do not expel liquids. Such treatment may be advantageously applied using a probe with electrodes mounted thereon. The electrodes are preferably spring electrodes which extend (radially) from the probe to assure good contact with the intestinal wall. This treatment is also useful for patients have a chronic irritated bowel, such as patients using strong medication and AIDS patients. In patients with a chronic problem, electrodes are preferably implanted on the outside of portions of the GI tract.

Another aspect of the present invention relates to increasing the contractility of at least a portion of GI tract 22, typically, to compensate for a medical conditions where the contractility of at least a portion of GI tract 22 is reduced to below normal levels. Such conditions are typical in older patients. Subnormal contraction forces are also found in patients in whom a portion of the bowel is denervated, in particular, in patients having Aclazia (acquired or chronic) and in other disorders such as diffuse systemic sclerosis, diabetic enteropathy and primary visceral myopathies. In such conditions, the non-excitatory electric field is preferably applied using wire electrodes which are either attached to the inside of GI tract 22, implanted in the muscle of GI tract 22 itself and/or using electrodes which are implanted on the outside surface of GI tract 22. Preferably, such electrodes are implanted by advancing a surgical probe along the outside of GI tract 22 and attaching electrodes at locations along the outside of the tract. Alternatively, a plurality of encapsulated controllers may be implanted at a plurality of points along GI tract 22. Each encapsulated controller includes a power source, electrodes and a controller which can be activated by external command to apply a non-excitatory field. Alternatively, each such encapsulated controller comprises an induction coil which converts RF radiation, which is transmitted to the coil from an external source, to a non-excitatory electric field.

Another aspect of the present invention relates to simultaneously applying several different types of control so as to achieve more precise control of the activation profile of GI tract 22. In one preferred embodiment of the invention, the motility of small intestine 27 and/or large intestine 29 is increased by inhibiting a returning wave. In a normally activated intestine, there is a forward wave which advances food matter in the intestine and also a returning wave, which causes the food to retreat along the intestine and assists in churning the food. In this preferred embodiment of the invention, the forward wave is not inhibited and the returning wave is inhibited so as to allow greater motility. Preferably, the returning wave is inhibited at its origin, the end of the intestine, by applying a fence at the location. FIG. 2 shows a controller 46 which applied a fence 48 at the end of small intestine 27. Preferably, controller 46 uses a sensor 52 and/or a sensor 50 to detect the forward wave and/or the returning wave, either by their electrical activity or by their mechanical action. In a preferred embodiment of the invention, fence 48 is synchronized to the forward wave and applied only enough time to block the returning wave. Controller 46 is preferably inserted using an endoscope, preferably, from inside the small intestine.

In accordance with another preferred embodiment of the invention, electrical control is used to advance a stuck bolus 56. To advance bolus 56, electrical control is applied to an area 60, forward of bolus 56, to relax it. An area 58, behind and around bolus 56 is preferably controlled to increase its contractility. A controller 54 may be permanently implanted at location 58, if, due to damage to nerve and/or muscle, boluses are expected to be stuck at this location. In a preferred embodiment of the invention, a significant portion of GI tract 22 is wired. A plurality of sensors are placed along the portion to detect a bolus in the portion. Thereafter, the above described method for advancing the bolus is applied at the detected location. The plurality of sensors may be impedance sensors, which preferably use the same electrodes as the field applying electrodes.

Figure 3:
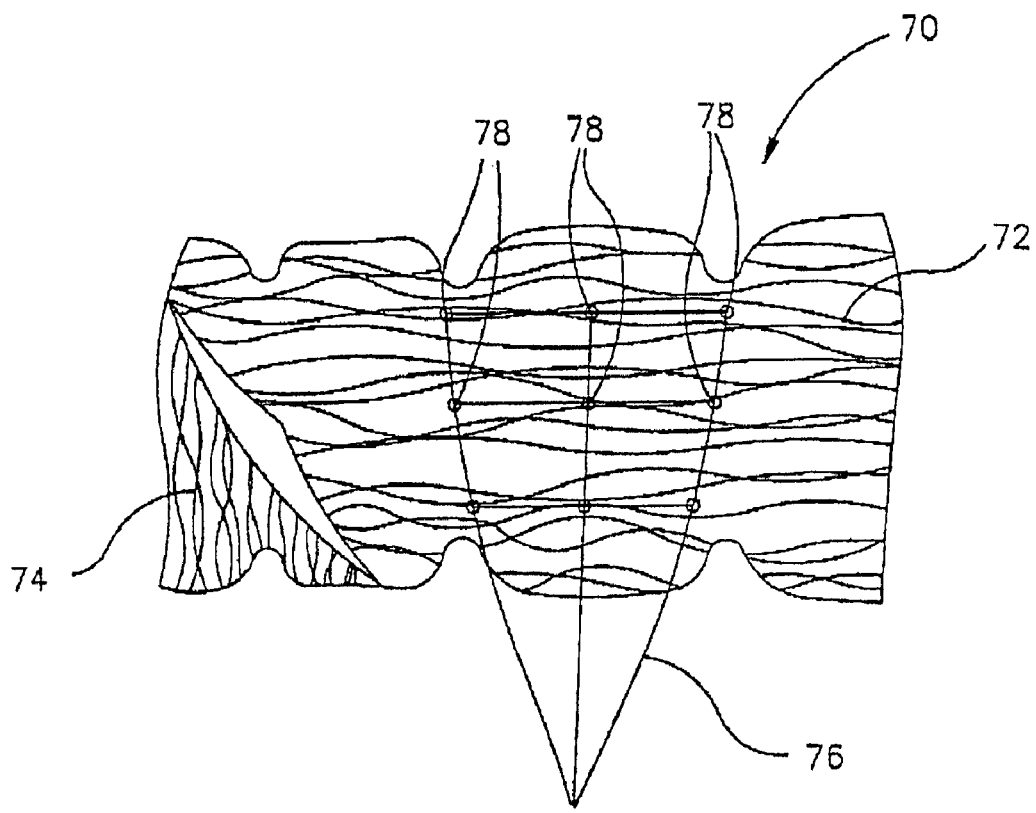
FIG. 3 is a partial cut-through schematic illustration of a laid-open portion of the GI tract, showing the orientation of smooth muscle fibers of the GI tract.

FIG. 3 is a partial cut-through schematic illustration of a laid-open portion 72 of GI tract 22, showing the orientation of smooth muscle fibers of the GI tract. GI tract 22 is typically composed of three muscle layers, a thin, electrically conducting layer (not shown), a inner layer 72 of fibers aligned generally along the length of GI tract 22 and an outer layer 74 of fibers aligned generally perpendicular to the fibers in layer 72. Layer 72 controls local changes in length of GI tract 22, while layer 74 controls local changes in diameter of GI tract 22.

In a preferred embodiment of the invention, a non-excitatory electrical field is selectively applied either to layer 72 or to layer 74, to either increase or decrease the local force of contraction. This selectivity may be achieved by aligning the direction of the electric field either in parallel to fibers in layer 72 or in parallel to fibers in layer 74. It should be noted that this type of selectivity is not possible when using an excitatory electric field, since such a field excites both layers 72 and 74.

In a preferred embodiment of the invention, a net electrode 76, having a plurality of individual electrodes 78, is used to affect this selectivity. If the net is placed so that its main axes are parallel to the fiber directions, an electrical field, having a direction parallel to one of the layers may be generated by choosing selected ones of electrodes 78. Ones of electrodes 78 can also be selected to apply a field which is diagonal to fibers in both layers. Alternatively or additionally, electrodes 78 are alternatively electrified, so that electric fields in both directions are alternatively applied. In particular, an inhibitory field may be applied in one direction while a contractility increasing field may be applied in the perpendicular direction. As can be appreciated, electrodes 78 may also be used to supply a pacing signal. In a preferred embodiment of the invention, electrodes 78 are also used to sense local electrical activity so as to better time the non-excitatory field.

Another type of electrode which is preferred for use in controlling smooth muscle, is an elongated electrode which is useful for applying an inhibiting electrical field, to create a fence. The propagation of an activation signal is most advantageously controlled (increased or decreased) by applying an electric field which is parallel to the fibers in the innermost layer of muscle, since that muscle layer conducts the activation signal. The propagation of the activation signal may be increased by applying a contractility enhancing electric field to the inner layer. Another method of selectively applying an electric field to only one layer is to insert the electrodes into the muscle, between the layers, so that substantially only one layer is inside the field.

Various apparatus for and methodologies for applying a non-excitatory electric field to cardiac muscle are described in six PCT applications, filed by applicant New Technologies (SA-YSY) Ltd. et al., in the Israel receiving office: PCT application PCT/IL97/00012, "Electrical Muscle Controller", filed Jan. 8, 1997, and five PCT applications filed on Jul. 9, 1997: PCT/IL97/00231, "Apparatus and Methods for Controlling the Contractility of Muscles", PCT/IL97/00232, "Drug-Device Combination for Controlling the Contractility of Muscles", PCT/IL97/00233, "Fencing of Cardiac Muscle", PCT/IL97/00235 "Cardiac Output Controller" and PCT/IL97/00236, "Cardiac Output Enhanced Pacemaker", the disclosures of which are incorporated herein by reference. In particular, these PCT applications describe various waveforms which may be used for applying non-excitatory electric fields, including, DC fields, AC fields, unipolar and bipolar fields and combinations of such fields. Further, PCT/IL97/00012 also describes the possibility of using light radiation and RF radiation to affect calcium transfer in cardiac muscle cells and thereby affect their force of contraction. These apparatus may be adapted, in accordance with preferred embodiments of the present invention to supply non-excitatory electric fields to smooth muscles.

When adapting the apparatus described herein to a particular physiology, it is expected that the amplitudes, delays and frequencies of the non-excitatory may need to be adapted. In a preferred embodiment of the invention, the apparatus is programmable by RF radiation. Thus, it can be implanted and different sets of pulse parameters may be tested to determine an optimal set. Additionally, the parameters may need to be adjusted after a time, due to adaptation of the controlled muscle, changes in impedance of the electrodes or to change the function of the controller.

As will be appreciated, some patients will require only a short course of treatment, while other patients will require a longer course, in some cases, a permanent treatment will be required. In a preferred embodiment of the invention, apparatus, as described herein is adapted to be implanted in the body, Alternatively, such apparatus is adapted to be inserted in the body, for a shorter period of time, such as under a month. This adaptation may provide for using different materials for the electrodes and for a different tradeoff between battery life and degree of control. Alternatively, such apparatus is adapted to be external to the body, either carried by the patient or free-standing. Preferably, at least the electrodes are implanted in the body or inserted in a body lumen.

It should also be noted that the activity of smooth muscles is also modified by their tension. In a preferred embodiment of the invention, a controller for smooth muscle includes sensors which measure the tension in the muscle and modifies the applied field responsive to the measured tension. Preferably, the tension is measured on the outside of the lumen of the smooth muscle. Alternatively or additionally, the tension is measured inside the lumen formed by the smooth muscle. Alternatively or additionally, the tension is measured inside the smooth muscle.

In a preferred embodiment of the invention, the orientation and polarity of the electric field relative to the muscle fibers are also varied to determine an optimal orientation and/or polarity which effect the desired control on the muscle. It should be noted that the two perpendicular muscle layers have different characteristics, such as resting tension, and, probably, a different response to the non-excitatory field. In a preferred embodiment of the invention, various orientations of the electric field to the muscle fibers, such as 0°, 5°, 10°, 30° and 45°, are tested without moving the electrodes. This is preferably achieved using a net-type electrode, where each junction of the net may be individually electrified. Thus substantially any effective field direction and polarity may be tested without moving the electrodes. Such a net electrode can also be used as a sensor net to more precisely determine the propagation direction of an activation front, as this propagation direction will generally be perpendicular to isochronal lines which mark equal activation times. In addition, changes in the activation profile, such as the effect of the controlling fields and/or arrhythmias can be detected from changes in the electrical signals sensed at the plurality of junctions of the net. In addition, mechanical activity may be localized by impedance measurement between individual ones of the junctions, either neighboring junctions, in which case characteristics of the muscle are measured or junctions which are on opposite sides of the smooth muscle, in which case occupancy of the GI tract may be determined.

It should be noted that the frequency of contraction of smooth muscle is usually much lower than cardiac muscle, enabling the use of simpler electronics and slower-responding power sources, for controlling smooth muscle. Furthermore, the propagation time along smooth muscle is usually much slower than for cardiac muscle. As a result, several seconds may pass between the activation time at one location and the activation time at a second location. Thus, to ensure a proper delay between local activation and local application of a non-excitatory field, local determination of activation time is especially preferred for smooth muscle control. Such local determination is preferably performed by local sensing, however, in other preferred embodiment of the invention, the local activation time is calculated using an estimated propagation velocity.

Figure 4:
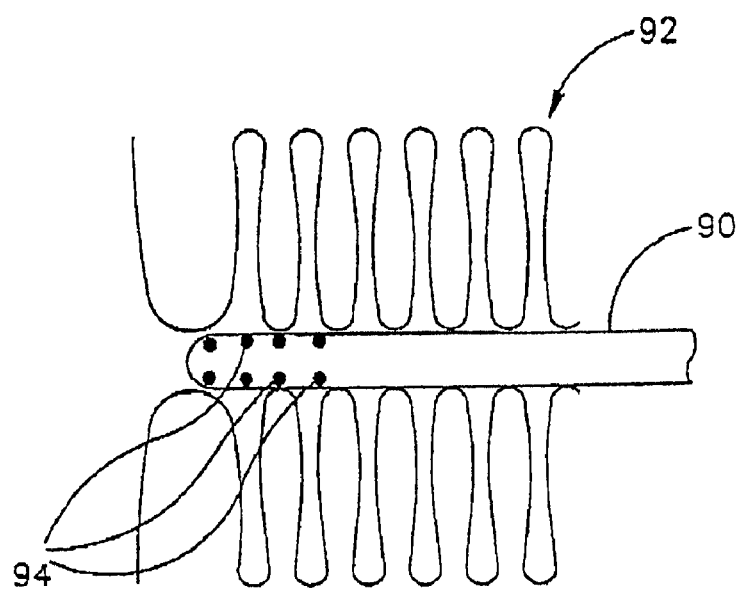
FIG. 4 illustrates a method of advancing a colonoscope using local control of the GI tract.

FIG. 4 illustrates a method of advancing a colonoscope 90 using local control of a portion 92 of GI tract 22. As minimally invasive procedures gain acceptance, periodic examination of the large intestine, using a colonoscope and of the small intestine, using an endoscope are becoming more common. In colon examination, the colonoscope is inserted into the anus and advanced along the colon. Periodically, the advance is stopped and the colon, surrounding the tip of the colonoscope, is inflated using air, so as to aid the advance of the colonoscope and to aid the examination of the colon wall. Drugs which relax the colon are usually administered to the patient prior to the examination.

In accordance with a preferred embodiment of the invention, a colonoscope 90 has a plurality of electrodes 94 at least at its tip. In a preferred embodiment of the invention, these electrodes are used to apply a relaxing electric field to the colon and thus, reduce the air pressure required to inflate it. In addition, such relaxing reduces the force required to advance the colonoscope, thereby reducing the danger of perforation. In a preferred embodiment of the invention, the electrodes are extendible from the tip of colonoscope 90 so that they can engage colon portion 92 even when it is inflated. Preferably, the electrodes can be temporarily hooked onto colon portion 92.

In accordance with another preferred embodiment of the invention, electrodes 94 are electrified to as to cause colon portion 92 itself to advance or to aid in the advance, of colonoscope 90. This advance may be achieved in one of two ways, either by blocking the forward wave and allowing the returning wave to advance colonoscope 90 or by selectively exciting muscles fibers in layers 72 and 74 (FIG. 3) so as to advance the colonoscope. One regimen of selective excitation includes: controlling layer 74 to more firmly grasp colonoscope 90 at its tip and exciting layer 72 to advance colonoscope 92. The order of excitation and the point from which the colon is excited, will, to a great measure, determine the direction of transport of colonoscope 92. Preferably, additional electrodes along colonoscope 90 (not shown) are used either to perform the same advancing action or to relax layer 74 along the length of colonoscope 92, to aid its advance. Selective excitation of a particular orientation of muscle fibers may be achieved by first inhibiting the other orientation of muscle fibers and then applying an excitatory stimulus. Retracting the colonoscope may be assisted by pacing colon potion 92 at the tip of colonoscope 90, so as to use the natural rhythm of colon portion 92 to retract colonoscope 90.

As can be appreciated, what has been described for a colonoscope applies equally to an endoscope, especially for retracting it. In a preferred embodiment of the invention, colonoscope 90 includes electrodes which apply a fencing field which blocks any local excitations from propagating to the rest of GI tract 22.

In accordance with another preferred embodiment of the invention, an endoscope which is used for entry into the bile duct, includes electrodes at its tip to apply a relaxing electric field, so as to enlarge the sphincter from the bile duct into the intestines. Preferably, such enlargement, when applied by a device which does not obstruct the bile duct, is used in conjunction with treatments for destroying gall bladder stones, to aid the exit of broken fragments of stone into the intestines. Alternatively, such a device is used to excite and/or increase the contractility of the bile duct to aid in the transport of such stones and/or to aid in its normal functioning. A non-obstructing device may be implanted externally to the gall bladder duct, such as inside small intestine 27 and only the leads for the electrodes need be in the duct. Alternatively, also the leads are implanted external to the duct.

Figure 5:
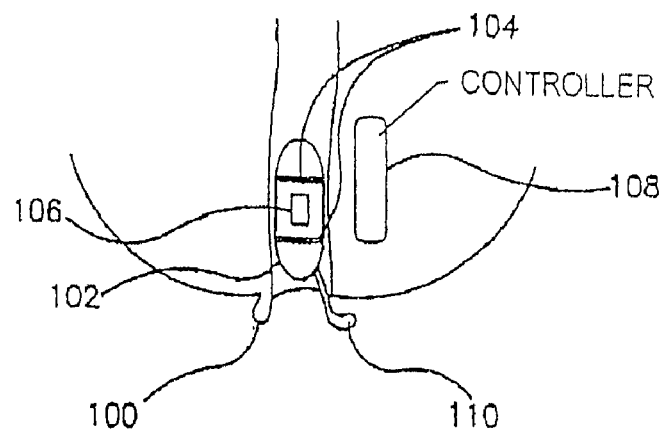
FIG. 5 is a schematic illustration of a capsule for treatment of hemorrhoids in accordance with a preferred embodiment of the present invention.

FIG. 5 is a schematic illustration of a capsule 102 for treatment of a hemorrhoid 100 in accordance with a preferred embodiment of the present invention. It has recently been determined that a major cause of hemorrhoids and a major factor in the non-healing of hemorrhoids and anal fissures is increased tension in the lower colon. The increased tension reduces the flow of blood, delaying healing and, at the same time, causing pain. It should be noted that tension in the lower part of the colon blocks blood from the rectal area, i.e., at some distance thereof. Topically applied Nitroglycerin (both at the hemorrhoids and inside the colon) has been suggested for reducing the tension in the lower colon. However, this drug has several side effects, such as dizziness. In accordance with a preferred embodiment of the invention, capsule 102 is inserted into the lower colon, where it applies relaxing electric fields, which either completely inhibit local contraction or at least, reduce it. Capsule 102 preferably includes a plurality of electrodes 104, a power supply 106 for electrifying the electrodes and, preferably, an attachment 110 for easy removal of capsule 102. Preferably, capsule 102 senses, using a pressure transducer (not shown) abnormal pressures in the colon and applies a relaxing electrical field only at those times or after such abnormal pressure has continued for a significant period of time. Alternatively or additionally, a tension sensor and/or an electrical activity sensor are used to sense the local activity of the colon.

In a preferred embodiment of the invention, suitable for female patients, capsule 102 is adapted to be inserted into a vagina and apply an electric field which affects the lower colon. Preferably, electrodes 104 are arranged so that the field is applied asymmetrically and mostly in the direction of the colon, since it is generally undesirable to effect a relaxing field on the muscles of the bladder or on the rectal sphincter. Thus, electrodes 104 are preferably arranged only on one side of capsule 102. Capsule 102 preferably includes a marking so that the patient will insert it in the proper orientation. Alternatively to using a capsule, a controller 108 may be implanted outside the colon.

Figure 6:
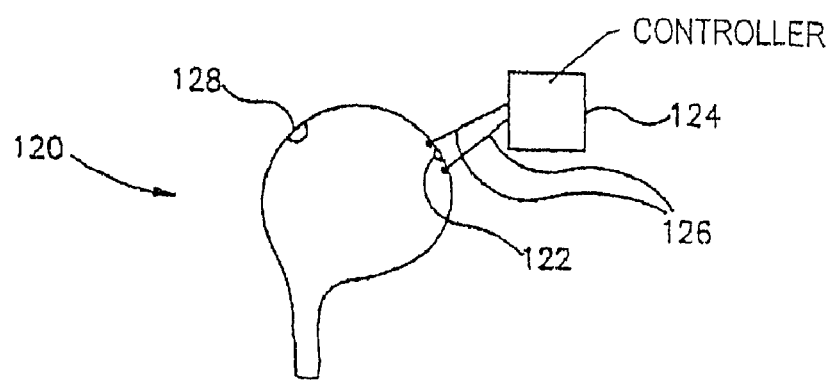
FIG. 6 is a schematic diagram of a uterus, illustrating applying local inhibitory electric fields to small portions of the uterus, in accordance with a preferred embodiment of the present invention.

FIG. 6 is a schematic diagram of a uterus 120, illustrating applying local inhibitory electric fields to small portions of thereof. Undesirable electrical activity in the uterus may induce premature labor in women. It is hypothesized that such undesirable electrical activity may, in many cases be cause by small regions of tissue, for example, near fibroids or myomas, where the stretching of the uterus may be maximal, or at inflamed locations. Unlike the heart, it may not be desirable to ablate portions of the uterus, as this may reduce the fertility and/or may irreversibly damage the uterus. In a preferred embodiment of the invention, electrical excitation from a fibroid 122 is blocked from propagating by fencing the fibroid or by desensitizing fibroid 122 and tissue surrounding it. FIG. 6 shows a controller 124 which administers such non-excitatory electrical fields using a plurality of electrodes 126. Preferably controller 124 is external to uterus 120, but it is preferably implanted inside the body. However, in other embodiments of the invention, only electrodes 126 of controller 124 are inserted in the body, for example, using a laproscopic procedure. Electrodes which need to be inserted into the back of the uterus may be inserted through the intestines.

Areas of the uterus which might cause such premature electrical activity may include, inflamed tissue, scar tissue, fibroids and malformed portions of the uterus. These types of tissue may be detected either by visual inspection (using a hysteroscope) or, preferably, using an electrical mapping probe, as known in the art of electrophysiology. Such mapping may also be performed during pregnancy, in which case the electrodes may be implanted from inside the uterus, during, or shortly after the mapping procedure. The controller will then preferably be external to the body, or possibly, in the vagina.

It has been suggested that there is a small region of the uterus, shown in FIG. 6 as a region 128, which generates a pacing signal for the entire uterus, at least during labor. In a preferred embodiment of the invention, labor is delayed by selectively inhibiting this area or by fencing it in, using non-excitatory electrical fields.

One aspect of the present invention relates to providing a more exact control over the process of labor than is possible using drugs. Several situations, where the response time of drugs is not sufficient, the side effects too great or proper dosage is difficult to establish, include:

(a) stopping premature labor;
(b) stopping a labor where a cesarean section is indicated;
(c) situations where fine control of the force of contraction of the uterus is required;
(d) assisting a labor which is not advancing properly; and
(e) stopping labor from ever starting, where it is contra-indicated.
(f) dictating a preferred contraction profile during labor.

Figure 7:
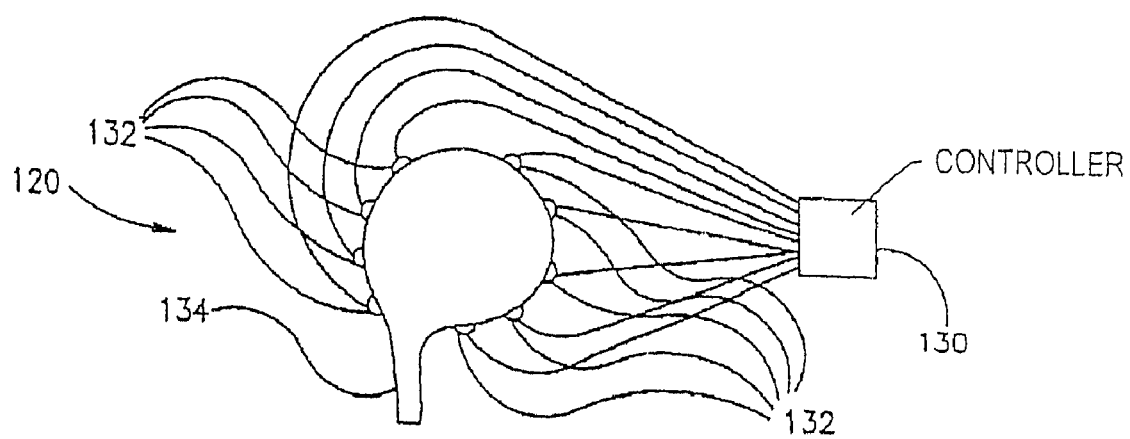
FIG. 7 illustrates an implantable multi-site stimulator/inhibitor, attached to a uterus, in accordance with a preferred embodiment of the invention.

FIG. 7 illustrates a implantable multi-site stimulator/inhibitor 130, attached to uterus 120, in accordance with a referred embodiment of the invention. Controller 130 includes a plurality of electrodes 132, preferably arranged to cover substantially all of uterus 120. These electrodes may be attached to the outside of uterus 120, for example during a laproscopic procedure. Alternatively electrodes 132 are attached to the inside of uterus 120, such as by an hysteroscopic procedure. Alternatively, these electrodes may be external to the body, such as on the skin, and possible, inserted in the intestines adjacent the uterus. In a preferred embodiment of the invention, electrodes 132 are implanted prior to the pregnancy, such as during a previous cesarean section and/or using a laproscopic procedure. Alternatively or additionally, electrodes to control smooth muscle are implanted in the blood vessels which adjacent the smooth muscle, such as the vessels which supply the smooth muscle. Preferably, the electrification of individual ones of electrodes 132 is timed to local electrical activity. Electrodes 132 can also be used to provide a stimulating signal, which will both induce and sustain labor.

In accordance with another preferred embodiment of the invention, multi-site pacing, is used to dictate a preferred activation (contraction) to the uterus. Preferably, multi-site pacing is complemented by local control of force of contraction (usually increase). Alternatively or additionally, fences are applied to the uterus, to channels the activation signals in a desired manner. It should be noted that fencing may be applied by itself, in combination with a single pacing location of in combination with multiple activation locations, in various preferred embodiments of the invention.

In accordance with a preferred embodiment of the invention, labor is advanced and/or assisted by increasing the force of contraction. The increase in the force of contraction causes a positive feedback effect which further increases the force of contraction. An increase in the force of contraction is also useful for assisting artificial abortions. In other situations, the force of contraction may need to be reduced or labor may have to be stopped completely, such as in cases of fetal distress or where there is danger of a rupture of the uterus, in which cases a cesarean section is to be performed. In cases of malformed or heavily scarred uteruses and in patients having a previous history of premature labor, controller 130 is preferably used to stop labor from ever occurring. Preferably, electrodes 132 are electrified to produce an inhibiting electrical field. Preferably, they are electrified only when controller 130 detects local electrical activity. Alternatively or additionally electrodes 132 are electrified responsive to the frequency of contraction of uterus 120.

In accordance with another preferred embodiment of the invention, a birth canal 134 and/or a cervix of uterus 120 is relaxed using a locally applied electric field, to aid in exiting of a baby therethrough. Alternatively, the force of contraction of the birth canal is increased prior to labor, to avoid a miscarriage. Alternatively or additionally, the muscles of the birth canal are also stimulated using excitatory signals to cause their contraction and avoid a miscarriage.

It should be appreciated that uterus 120 undergoes very significant changes in size over the course of a pregnancy. Thus, the leads of electrodes 132 are preferably made very flexible and elastic. In one preferred embodiment of the present invention, the leads are formed of a coiled wire, so that if the lead is stretched, the coil tightens, rather than break the wire. Preferably, the coil is wound about a flexible core. Preferably, the leads of electrodes 132 include weakened points, such that if strain of above a predetermined value is applied to the lead it will break at one of the preselected points, rather than damage tissue structures adjacent the lead.

In a preferred embodiment of the invention, each of electrodes 132 comprises an encapsulated power supply and controller 130 coordinates the individual electrodes using wireless communication. Thus, electrodes 132 do not need to be interconnected by wires. Alternatively, electrodes 132 are coordinate their electrification using techniques well known in the art of distributed computing and without a central controller. Alternatively to synchronizing their activity, each of electrodes 132 operates responsive to local activity.

Figure 8:
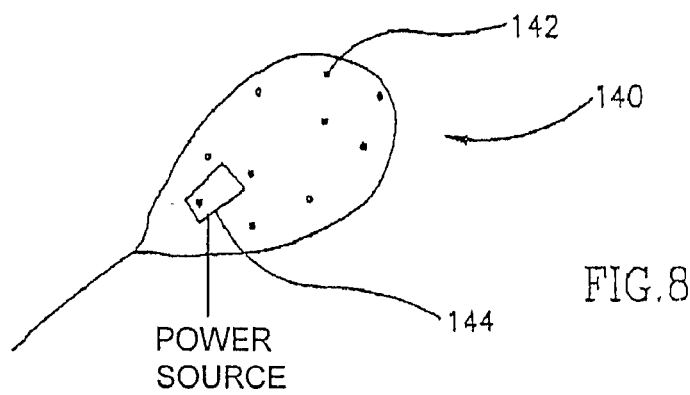
FIG. 8 illustrates a balloon-type insert for a uterus, for controlling cramps.

FIG. 8 illustrates a balloon-type insert 140 for uterus 120, for controlling cramps. Insert 140 comprises a plurality of electrodes 142, disposed on the outside of the device, which electrodes are electrified by a power source 144. Insert 140 is preferably inflatable to assure better contact with the inner wall of uterus 120. In a preferred mode of operation, various ones of electrodes 142 function as electrical activity sensors. Once such electrical activity is sensed, an inhibiting field is applied at those locations to prevent the future occurrence of electrical activation and/or to prevent its propagation. Alternatively, such a device continuously applies an inhibitory electrical field. In a preferred embodiment of the invention, the inhibitory electrical field is applied between electrodes 142 and an external electrode which is placed on the abdomen and/or on the back. Although point electrodes are shown in the figure, it should be appreciated that other forms of electrodes, such as elongated electrodes may also be used. Preferably, the device is removed from the body when cramps are not expected.

Figure 9:
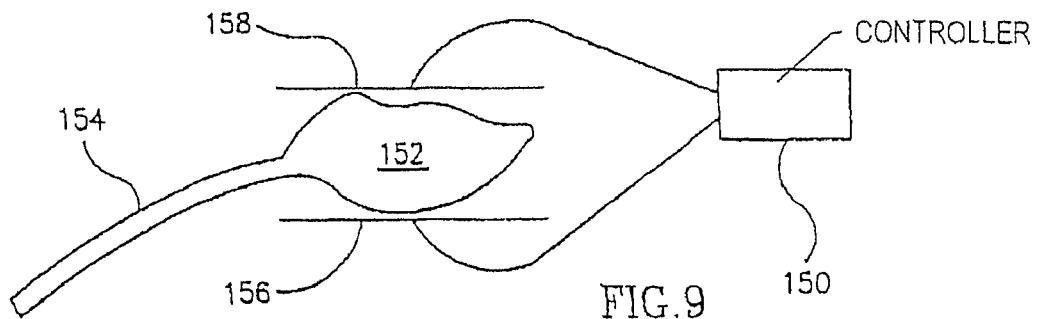
FIG. 9 illustrates a controller which modifies the output of a gland, such as the pancreas.

FIG. 9 shows a controller 150 which modifies the output of a gland, such as a pancreas 152. In some glands, such as pancreas 152, execration of hormones into a blood vessel 154 is meditated by electrical excitation of the hormone producing cells (beta islet cells in the pancreas). The electrical excitation, as in many smooth muscles, is initiated by chemical signals. In accordance with a preferred embodiment of the invention, the hormone execrating cells are desensitized so that they do not respond to these chemical signals, or, if some of the cells do respond, these cells cannot generate a propagating activation signal, since the surrounding cells are electrically deactivated. Thus, the amount of execrated hormone is reduced. This method is especially useful in diseases, such as tumors, where a gland over produces its hormone.

Controller 150 preferably includes an electrode 158 and, preferably, a second electrode 156 so as to create an electric field which inhibits or reduces the electrical activity of the hormone producing cells. The casing of controller 150 may be used as the second electrode, in this and in other of the above described preferred embodiments. As can be appreciated, the levels of hormone in the blood and the electrical activity of the hormone producing cells is rather difficult to detect using current technology. Thus, in a preferred embodiment of the invention, a substantially constant inhibitory electrical field is applied. Preferably, the polarity of the field is changed periodically, so as to prevent ionic-meditated damage and the ionization of electrodes 156 and 158. Alternatively, controller 150 may measure local electrical activity, hormone levels or it may measure a bodily indicator, such as glucose level, which is correlated with the hormone level and apply a voltage to electrodes 156 and 158, as indicated.

Figure 10:
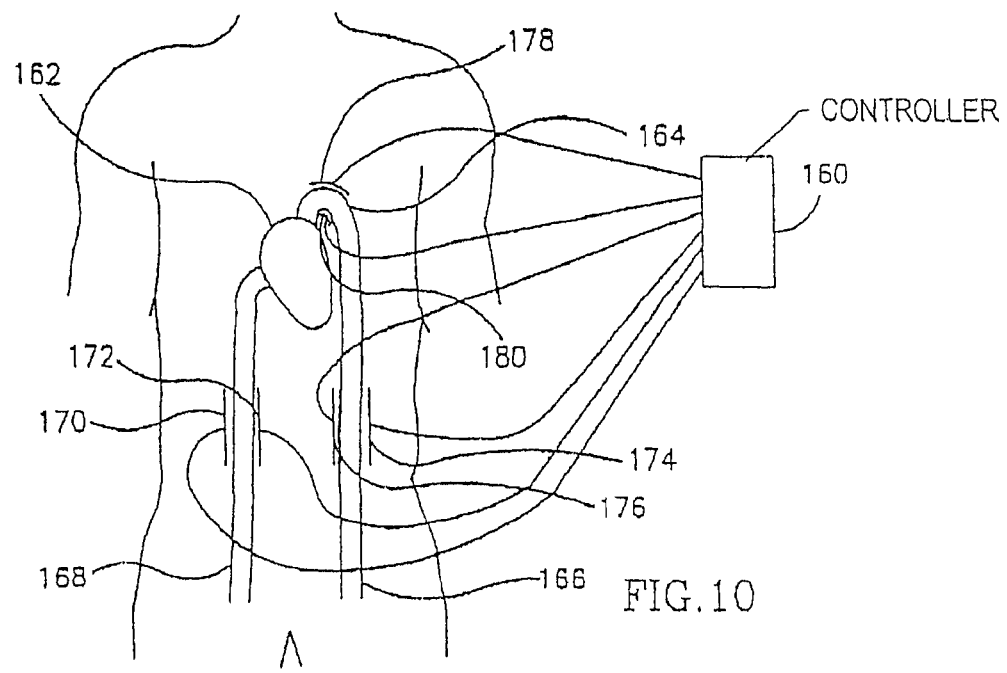
FIG. 10 illustrates a blood pressure and/or heart load controller, attached to major blood vessels, in accordance with a preferred embodiment of the invention.

Another aspect of the present invention relates to controlling blood pressure and/or other circulatory parameters such as the load on a heart. Preferably, the control is exerted in conjunction with the use of a cardiac controller, such as described in the above referenced PCT applications. FIG. 10 illustrates a blood pressure and/or heart load controller 160, attached to major blood vessels, in accordance with a preferred embodiment of the invention. A heart 162 receives blood from an abdominal vena cava 168 and pumps it to an aorta 164 and from there to an abdominal aorta 166. In the event of a spasm in aorta 164, it greatly constricts, increasing the afterload on the heart. In many cases this types of spasm will cause dizziness. In patients having constricted coronary arteries, the increased cardiac demand may also cause a painful episode of angina pectoris.

In accordance with a preferred embodiment of the invention, the afterload of heart 162 is momentarily reduced by relaxing large arteries. Alternatively or additionally, the preload of heart 162 is momentarily reduced by relaxing large veins. Reducing either the preload and/or the afterload, reduces the work demanded from heart 162 and will, in many cases, stop the pain of angina pectoris. Alternatively or additionally, the walls of the large blood vessels are relaxed in order to lower the blood pressure, during an acute episode of high blood pressure. Alternatively, the blood vessels may be constricted, such as during an acute episode of low blood pressure. Reducing the load on heart 162 is especially beneficial if practiced while extending the diastole of the left ventricle of heart 162, such as by extending the refractory periods of muscle cells therein, for example, as described in the above mentioned PCT applications.

The choice of the particular blood vessel to relax depends, inter alia, on the type of load which is desirable to reduce, on whether the hypertension is pulmonary or systemic and, in case of a spasm, if the vessel having a spasm has implanted electrodes.

In a preferred embodiment of the invention, the vessel in spasm is detected using by measuring changes in the impedance between the electrodes surrounding the blood vessel. Alternatively, rather than determining which vessel is in spasm, all wired blood vessels are relaxed.

In a preferred embodiment of the invention, controller 160 includes a pair of electrodes 170 and 172 for controlling abdominal vena cava 168. Alternatively or additionally, controller 160 includes a pair of electrodes 174 and 176 for controlling the abdominal aorta. Alternatively or additionally, controller 160 includes a pair of electrode 178 and 180 for controlling the aorta, preferably, at or about the aortic arch. In a preferred embodiment of the invention, the electrodes are net-type electrodes, since the muscle fibers in blood vessels are mostly oriented perpendicular to the direction of flow of blood and a field perpendicular to the blood flow direction is desirable. Alternatively, the electrodes are elongated electrodes, arranged parallel to the blood flow, to apply a field perpendicular to the blood flow, between pairs of electrodes. Preferably, controller 160 is externally controllable, so that a patient can activate it when he feels pain and/or dizziness. Alternatively or additionally, controller 160 includes a blood pressure sensor (not shown), for automated closed loop blood pressure control. Alternatively or additionally, controller 160 includes an ECG sensor or a blood flow sensor, so that the application of the fields to the vascular system may be synchronized to the cardiac rhythm. Preferably, controller 160 includes a fail-safe cutoff which prevents the patient from reducing or increasing the blood pressure beyond acceptable limits.

FIGS. 11-16 describe experiments which show that the force of contraction of a smooth muscle can be increased or decreased by application of non-excitatory electric fields directly to the muscle.

Male, New Zealand White rabbits (1-2 Kg body weight) were dissected and various portions of their GI tract were removed and used for the following experiments. The animals were anesthetized using pentobarbitone (Ceva, France), 60 mg/Kg body weight, by IV. The abdominal wall was opened to expose the abdominal viscera. Required portions of the GI tract were removed and placed in a cold (4° C.) oxygenated (95/5 $O_2$/$CO_2$) Krebs-Heseleit solution, containing (in mM): KCl 4.5, NaCl 118, NaHCO$_3$ 24, MgSO$_4$ 1.19. KH$_2$PO$_4$ 1.18, Glucose 11 and CaCl$_2$ 2.52). The removed portions were then further dissected in a dissection chamber (Hugo Sachs Electronik (HSE), Germany) to produce a single strip of GI muscle which was then placed in an organ bath. The organ bath is a type 813 (I-18E) by HSE and it includes a temperature controller type 319 and a force transducer type F30 with a 660 type amplifier. The elapsed time for the removal procedure is about 3-5 minutes.

Figure 11:
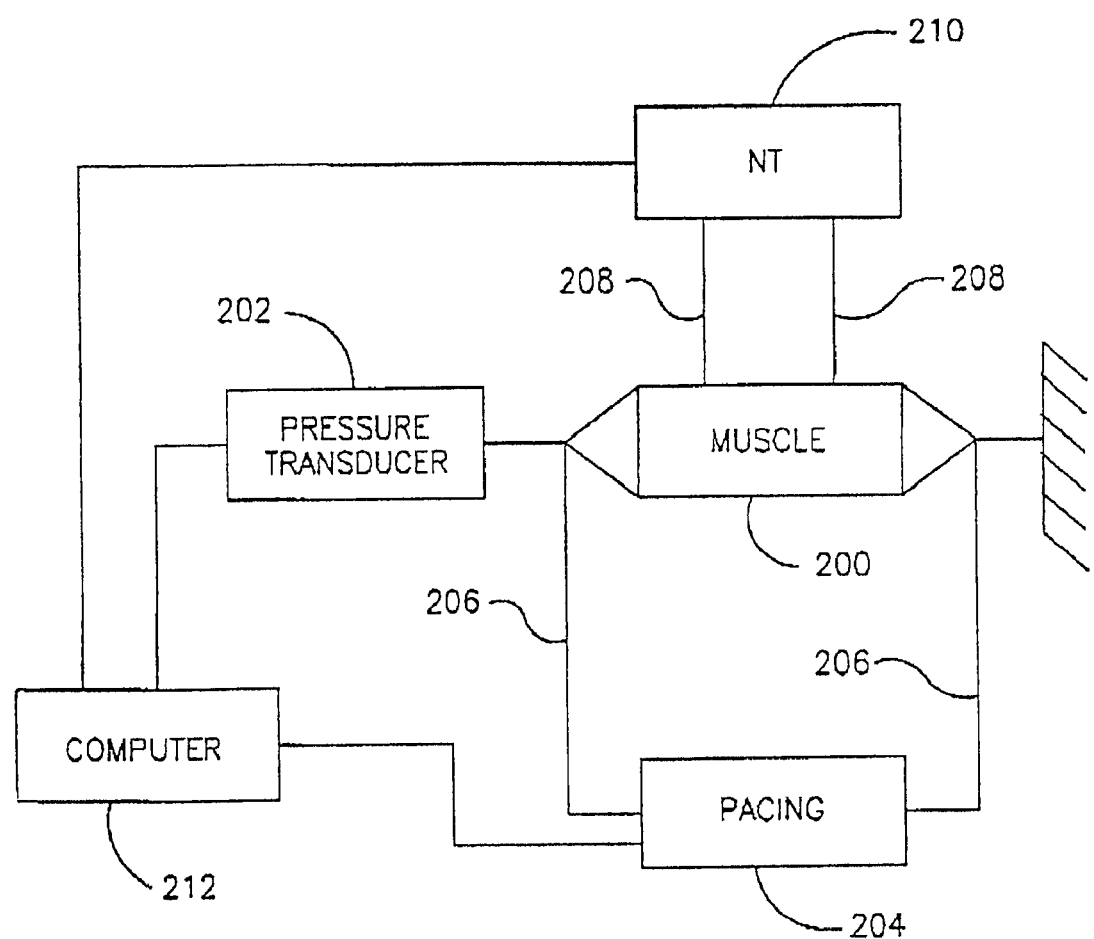
FIG. 11 is a schematic illustration of an experimental setup used to determine effects of a non-excitatory field on smooth muscle cells.

FIG. 11 is a schematic illustration of an experimental setup used to determine the effects of a non-excitatory field on smooth muscle cells. A GI muscle portion 200 is fixed in an organ bath chamber, one end is fixed to the chamber using a plastic clip, while the other end is hooked to a pressure transducer 202. The length of the GI muscle is adjusted to allow maximal isometric force. The organ bath is temperature controlled and the GI muscle is continuously perfused (7-12 ml/min) with the above described oxygenated solution, maintained at about 36.1° C. The muscle was allowed to remain in the organ bath for a 30 minutes equilibrium period prior to experimentation.

The organ bath includes two Ag—AgCl electrodes 206 which were used to apply a pacing pulse, where required by the experimental protocol. These electrodes were chlorodized before each experiment. The pacing stimuli was provided by a constant current source. The pacing waveform was a square wave pulse. A non-excitatory electric field was applied using carbon electrodes 208 (shaped from carbon rods provided by Goodfellow, UK) which were placed about 2-3 millimeters apart. The electrodes were electrified by a constant current source 210. The two constant current sources were home made current sources whose current level was modified by computer control. The output of these current sources was continuously monitored to verify that a constant current was produced. The entire experiment was controlled by a computer 212 and the data was acquired using dedicated data acquisition circuits, such as a PCI-MIO-16XE50 or an AT-MIO-16E-2 (National Instrument, USA). The organ bath was placed on an anti-vibration table (TMC, USA). Both the pacing current and the non-excitatory current were constant current pulses. The amplitude of the pacing is different between the following experiments, in the main pat, to counteract polarization of the electrodes. The delay of the non-excitatory field (NT current) is from the start of the pacing signal.

FIGS. 12-17 show experimental results using a section of GI tract from the Jejunum. The fields were applied and the transducer measured force were approximately along the direction of the GI tract. As described above, variations in the orientation can change the effect of the non-excitatory pulse. The polarity of the field was sometimes selected to cause a force increasing effect and sometimes to produce a force decreasing effect.

Figure 12:
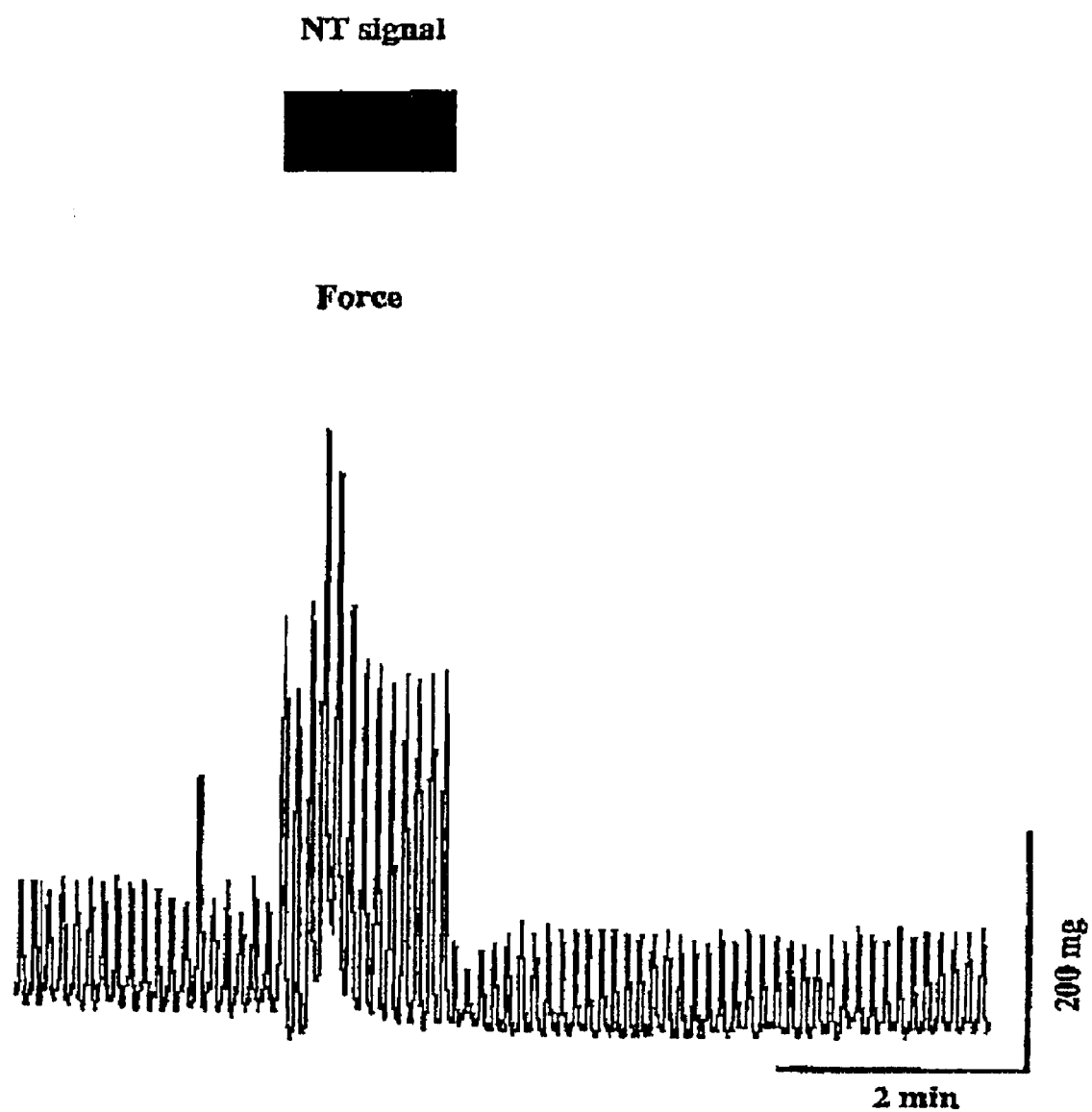
FIG. 12 is a graph of experimental results showing an increase in the force of contraction of a smooth muscle, as a result of the application of a non-excitatory electric field, in accordance with a preferred embodiment of the invention.

FIG. 12 is a graph of experimental results showing an increase in the force of contraction of a smooth muscle, as a result of the application of a non-excitatory electric field in accordance with a preferred embodiment of the invention. The non-excitatory field is shown as a full bar marked "NT."

In this experiment, the pacing was 0.15 Hz, 30 ms duration and 3 mA current. The non-excitatory field was a 200 ms current pulse at 10 mA applied at a delay of 50 ms after the pacing. As seen in FIG. 12, an increase of about 300% in the force of contraction was achieved.

FIGS. 13-16 are graph of experimental results showing a significant decrease in the force of contraction of a smooth muscle, as a result of the application of a non-excitatory electric field in accordance with a preferred embodiment of the invention.

Figure 13:
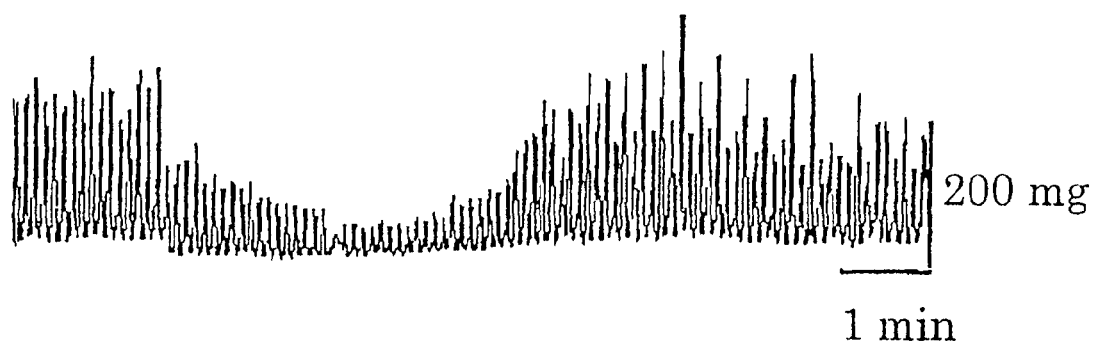
FIGS. 13-17 are graphs of experimental results each showing a significant decrease in the force of contraction of a smooth muscle, as a result of the application of a non-excitatory electric field in accordance with a preferred embodiment of the invention.

In FIG. 13, a 70% reduction in force of contraction was achieved. The pacing was the same as in FIG. 12, while the non-excitatory pulse was applied for 100 ms, at a 100 ms delay after the pacing and at 10 mA. It should be noted that the effect of the non-excitatory field lasted for a while after the removal thereof. In addition, the non-excitatory field also reduced the base tone of the muscle, i.e., it relaxed it.

Figure 14:
Figure 14:
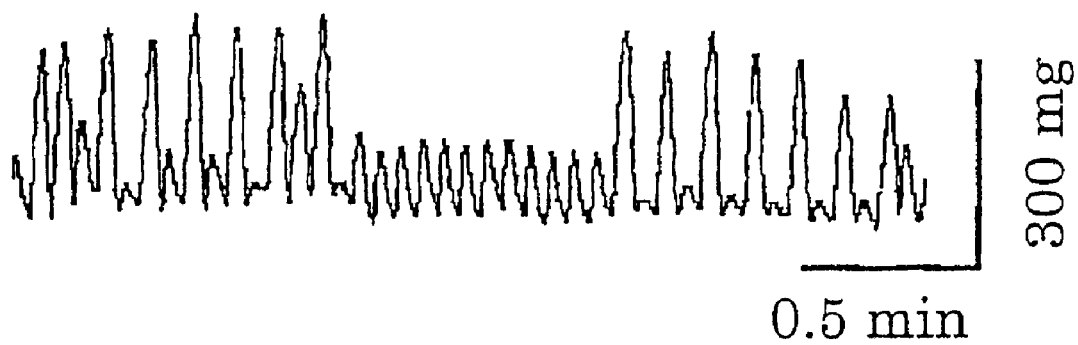

In FIG. 14, a substantial reduction in force of contraction was achieved. The pacing was faster than in FIGS. 12 and 13: 0.25 Hz, 30 ms duration and 10 mA amplitude. The non-excitatory pulse was applied for 50 ms, at a 50 ms delay after the pacing and at a 10 mA amplitude. In this experiment too, a reduction in muscle tone is observed.

Figure 15:
Figure 15:
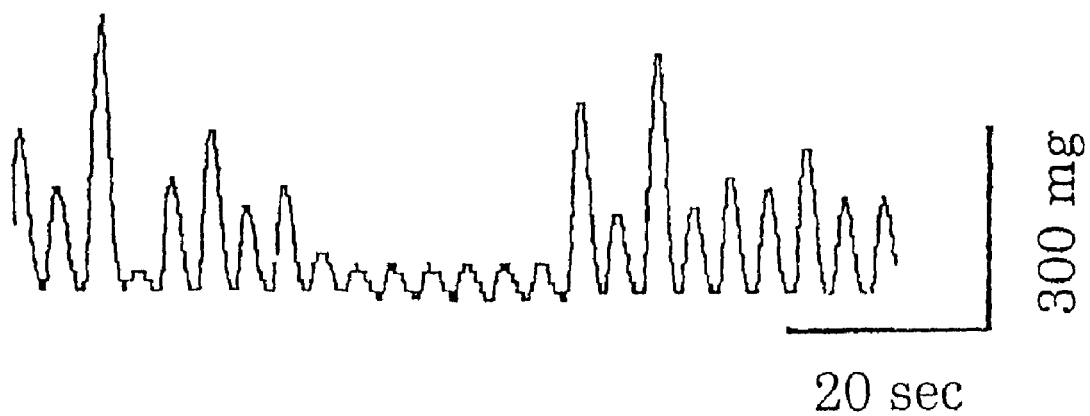

In FIG. 15, a substantial reduction in force of contraction was achieved. The pacing was different from that of FIG. 14: 0.25 Hz, 30 ms duration and 3 mA amplitude. The non-excitatory pulse was applied for 60 ms, at a 200 ms delay after the pacing and at 10 mA. In this experiment too, a reduction in muscle tone is observed.

Figure 16:
Figure 16:
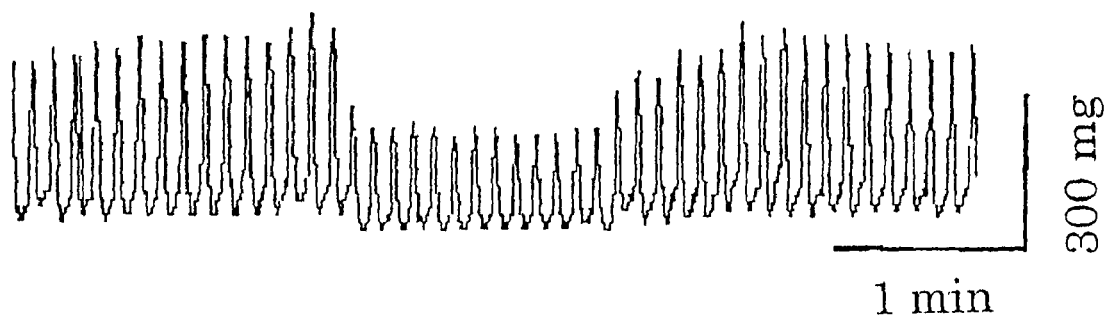

In FIG. 16, a substantial reduction in force of contraction was achieved. The pacing was similar to that of FIGS. 12 and 13: 0.15 Hz, 30 ms duration and 3 mA amplitude. The non-excitatory pulse was applied for 100 ms, at a 50 ms delay after the pacing and at 10 mA. In this experiment too, a reduction in muscle tone is observed.

Figure 17:
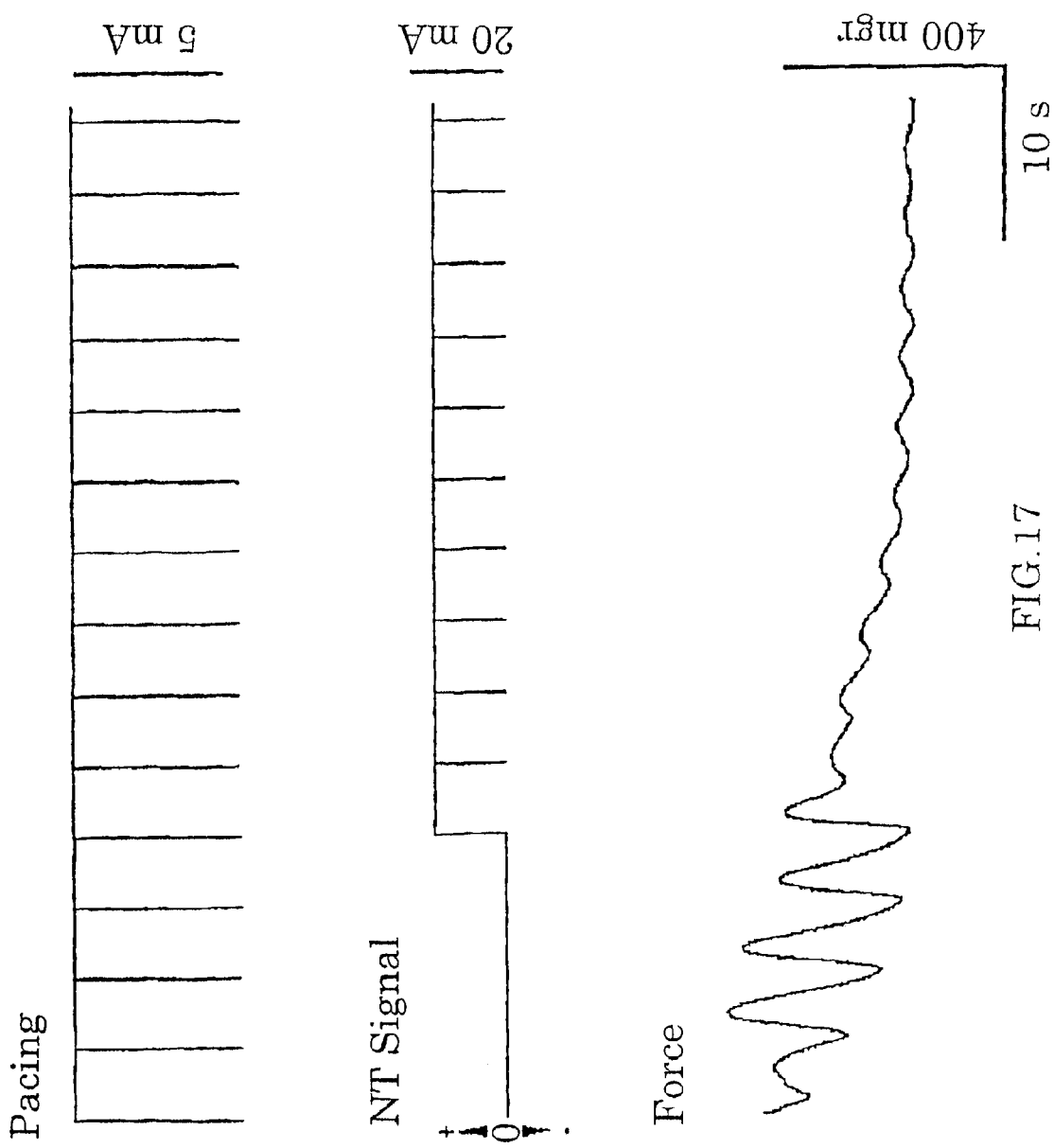

In FIG. 17, a substantial reduction in force of contraction was achieved using a substantially constant non-excitatory field. The pacing was 0.25 Hz, 2 ms duration and 5 mA amplitude. The non-excitatory pulse was applied for 3990 ms, at a 5 ms delay after the pacing and at an amplitude of 15 mA. A nearly complete blockage of contraction is observed of In this experiment too, a reduction in muscle tone is observed.

Figure 18:
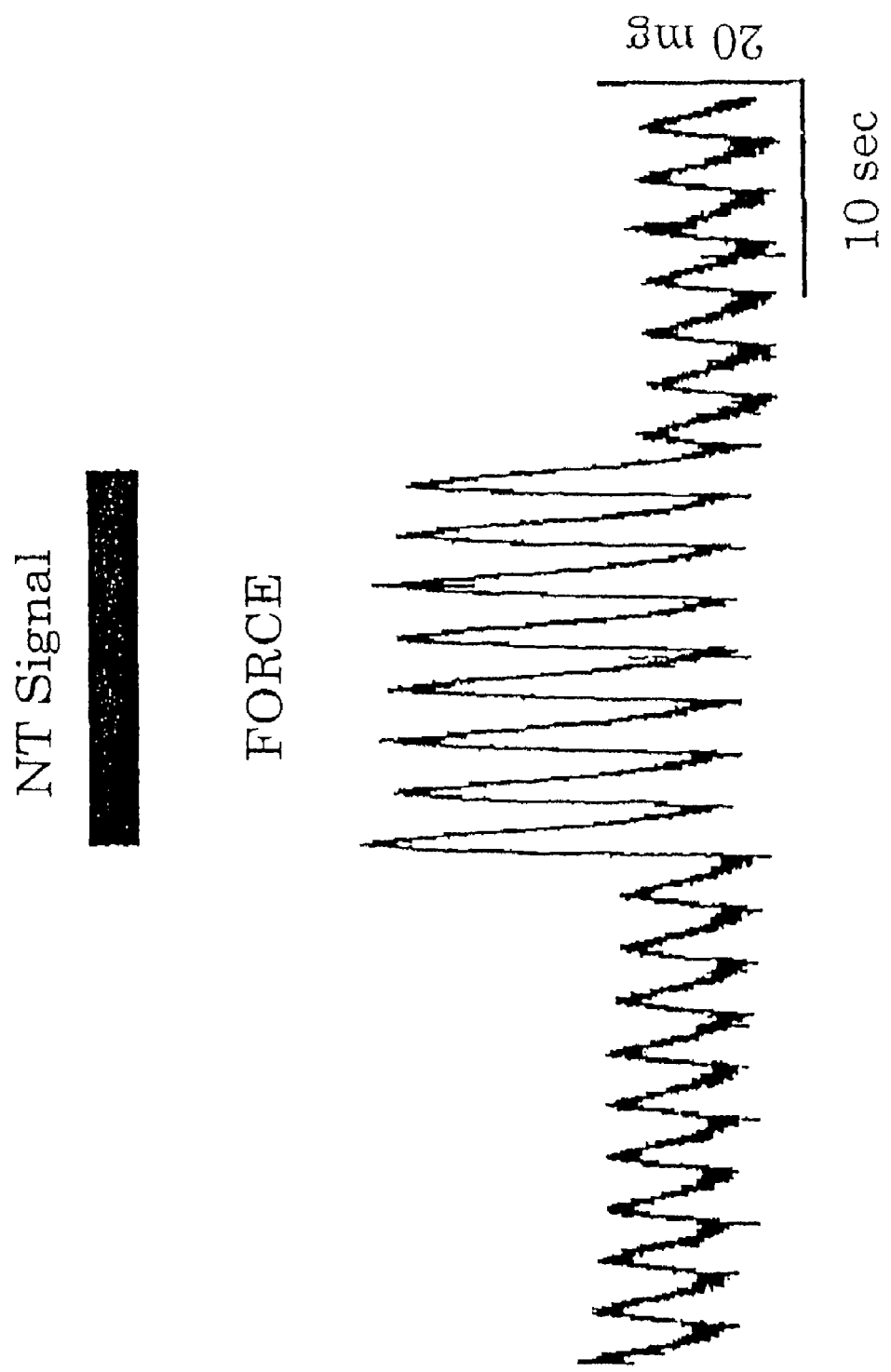
FIG. 18 is a graph of experimental results showing an increase in the force of contraction of a smooth muscle of the urine bladder, as a result of the application of a non-excitatory electric field, in accordance with a preferred embodiment of the invention.

FIG. 18 is a graph of experimental results showing an increase in the force of contraction of a smooth muscle of a urine bladder, as a result of the application of a non-excitatory electric field, in accordance with a preferred embodiment of the invention. The bladder segment was prepared as described above. It was paced at 0.2 Hz, 30 ms duration and 6 mA amplitude. The non-excitatory field was a 60 ms duration pulse applied at a 30 ms delay after pacing and having an amplitude of 10 mA. It should be noted that the resting tension of the bladder segment also increased as a result of applying the non-excitatory field.

Figure 19:
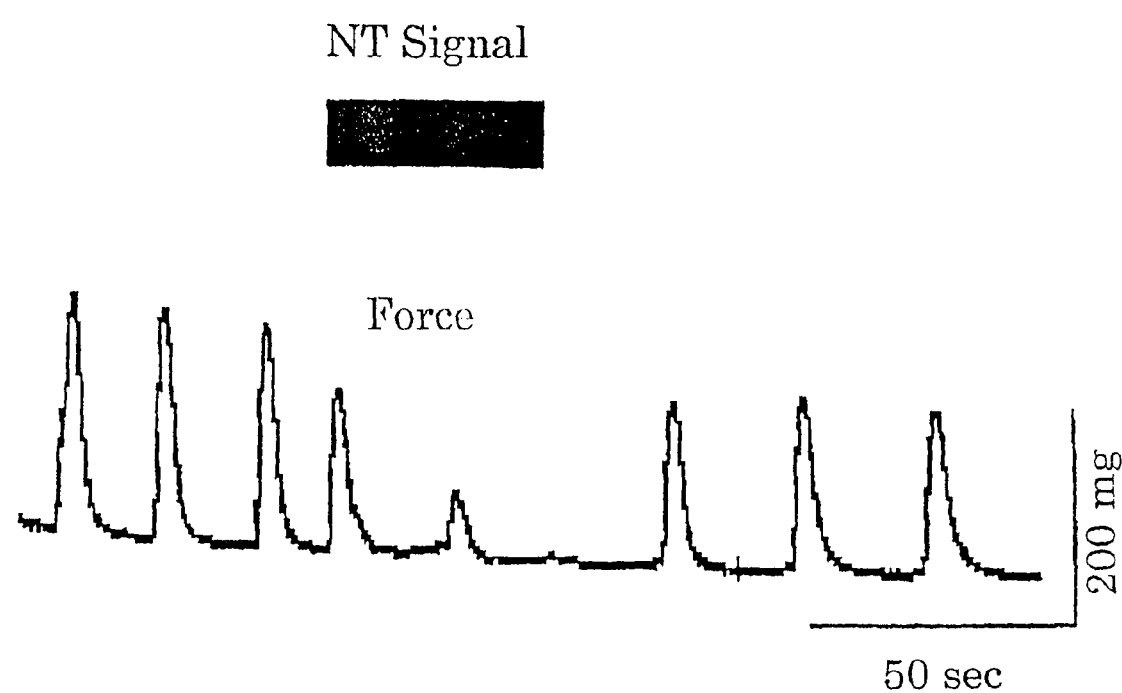
FIG. 19 is a graph of experimental results showing a decrease in the force of contraction of a smooth muscle of an unpaced uterus, as a result of the application of a non-excitatory electric field, in accordance with a preferred embodiment of the invention.

FIG. 19 is a graph of experimental results showing an increase in the force of contraction of a smooth muscle of a rabbit uterus, as a result of the application of a non-excitatory electric field, in accordance with a preferred embodiment of the invention. The uterus segment was prepared as described above. The muscle segment was not artificially paced, it was self paced. The non-excitatory field was a pulse of 20 ms duration, 10 mA amplitude and applied at 0.2 Hz. It should be noted that not only was the force of contraction significantly reduced, after about 30 seconds of application of the non-excitatory field, the contraction of the tissue was apparently completely inhibited. The effects of the field also lasted for a short time after the removal thereof.

It will be appreciated by a person skilled in the art, that although the present invention has been described with reference to the preferred embodiments, the scope of the invention is not limited by what has thus far been described. In particular adaptation of the above described durations, amplitudes and delays of non-excitatory signals to particular patients is considered to be within the ability of a man of the art and also within the scope of the present invention. Thus, the scope of the present invention is limited only by the claims which follow.

The invention claimed is:

1. Apparatus comprising:
    at least one implantable electrode adapted to be placed adjacent to a portion of smooth muscle; and
    a controller for electrifying said implantable electrode with a non-excitatory electric field which does not generate excitation of said smooth muscle, wherein said non-excitatory electric field affects the activity of said smooth muscle in a manner that controls a level of a chemical in the blood stream.

2. The apparatus according to claim 1, comprising a sensor for measuring a level of said chemical in a blood stream.

3. The apparatus according to claim 2, wherein said controller electrifies said implantable electrode with said non-excitatory electric field, responsive to the measured level.

4. The apparatus according to claim 3, wherein said chemical is glucose.

5. The apparatus according claim 1, wherein said chemical is a hormone.

6. The apparatus according to claim 5, wherein said hormone is insulin.

7. The apparatus according to claim 1, wherein said chemical is glucose.

8. The apparatus according to claim 1, wherein said at least one implantable electrode is configured to be located in the GI tract.

9. The apparatus according to claim 8, wherein said at least one implantable electrode is configured to be located on the stomach.

10. The apparatus according to claim 1, wherein said implantable electrode is configured to be located adjacent to the pancreas.

11. A method for controlling the level of a chemical in the blood of a patient, comprising:
    implanting at least one electrode adjacent to a portion of smooth muscle or a of said patient; and electrifying said electrode with a non-excitatory electric field which does not generate excitation of said smooth muscle, wherein said non-excitatory electric field affects the activity of said smooth muscle in thereby controlling the level of said chemical in the patient's blood stream.

12. The method according to claim 11, comprising measuring a level of said chemical in a blood stream.

13. The method according to claim 12, wherein electrifying said electrode with said non-excitatory electric field is responsive to the measured level.

14. The method according to claim 13, wherein said chemical is glucose.

15. The method according to claim 11, wherein said chemical is a hormone.

16. The method according to claim 15, wherein said hormone is insulin.

17. The method according to claim 11, wherein said chemical is glucose.

18. The method according to claim 11, wherein said at least one electrode is located in the GI tract.

19. The method according to claim 11, said electrode is adjacent to the pancreas.

20. The method according to claim 11, wherein said at least one electrode is located inside the body of the patient and outside a portion of the GI tract.

21. A method for controlling the level of a chemical in the blood of a patient, comprising:
   placing at least one electrode adjacent to a portion of smooth muscle or a gland of said patient; and
   electrifying said electrode with a non-excitatory electric field which does not generate excitation of said smooth muscle or gland, wherein said non-excitatory electric field affects the activity of said smooth muscle or gland in thereby controlling the level of said chemical in the patient's blood stream,
   wherein said at least one electrode is located in the GI tract on the stomach.

* * * * *